(12) United States Patent
Solar et al.

(10) Patent No.: US 8,486,025 B2
(45) Date of Patent: Jul. 16, 2013

(54) SYSTEMS AND METHODS FOR TREATING A VESSEL USING FOCUSED FORCE

(76) Inventors: Ronald J. Solar, San Diego, CA (US); Yoav Shaked, Tzoran (IL)

(*) Notice: Subject to any disclaimer, the term of this patent is extended or adjusted under 35 U.S.C. 154(b) by 319 days.

(21) Appl. No.: 12/903,111

(22) Filed: Oct. 12, 2010

(65) Prior Publication Data

US 2011/0034949 A1    Feb. 10, 2011

Related U.S. Application Data

(63) Continuation-in-part of application No. 11/746,682, filed on May 10, 2007, now Pat. No. 7,901,378, which is a continuation-in-part of application No. 11/431,918, filed on May 11, 2006, now Pat. No. 7,780,715.

(30) Foreign Application Priority Data

Oct. 3, 2006   (IL) ................. PCT/IL2006/001150

(51) Int. Cl.
*A61M 5/178*   (2006.01)

(52) U.S. Cl.
USPC .................................. 604/164.13

(58) Field of Classification Search
USPC .................................. 604/164.13
See application file for complete search history.

(56) References Cited

U.S. PATENT DOCUMENTS

| | | |
|---|---|---|
| 4,723,948 A | 2/1988 | Clark et al. |
| 4,906,241 A | 3/1990 | Noddin et al. |
| 4,917,088 A | 4/1990 | Crittenden |
| 4,983,167 A | 1/1991 | Sahota |
| 5,059,178 A | 10/1991 | Ya |
| 5,090,958 A | 2/1992 | Sahota |
| 5,147,377 A | 9/1992 | Sahota |
| 5,160,321 A | 11/1992 | Sahota |
| 5,267,958 A | 12/1993 | Buchbinder et al. |
| 5,267,960 A | 12/1993 | Hayman et al. |
| 5,320,605 A | 6/1994 | Sahota |
| 5,342,297 A | 8/1994 | Jang |
| 5,370,617 A | 12/1994 | Sahota |
| 5,376,074 A | 12/1994 | Buchbinder et al. |

(Continued)

FOREIGN PATENT DOCUMENTS

| | | |
|---|---|---|
| CN | 1051984 | 10/2012 |
| EP | 0492361 A1 | 7/1992 |

(Continued)

OTHER PUBLICATIONS

CN 200580011142.7 filed Mar. 3, 2005 Office Action dated Apr. 26, 2010.

(Continued)

*Primary Examiner* — Theodore Stigell
*Assistant Examiner* — Diva K Chander
(74) *Attorney, Agent, or Firm* — Rutan & Tucker, LLP

(57) ABSTRACT

A device for introduction into a body vessel includes a main elongated element, a balloon positioned at the main elongated element distal end, a distal connecting element positioned at the distal end of the balloon to receive a guidewire during use, and a longitudinally movable sheath positioned external to the main elongated element, a position of the sheath distal end with respect to the balloon defining an exposed portion of the balloon that expands when fluid is delivered to the balloon through the inflation lumen.

23 Claims, 16 Drawing Sheets

U.S. PATENT DOCUMENTS

| | | | |
|---|---|---|---|
| 5,383,853 | A | 1/1995 | Jung et al. |
| 5,395,332 | A | 3/1995 | Ressemann et al. |
| 5,413,557 | A | 5/1995 | Solar |
| 5,425,711 | A | 6/1995 | Ressemann et al. |
| 5,439,445 | A | 8/1995 | Kontos |
| 5,462,530 | A | 10/1995 | Jang |
| 5,479,938 | A | 1/1996 | Weier |
| 5,520,647 | A | 5/1996 | Solar |
| 5,522,818 | A | 6/1996 | Keith et al. |
| 5,534,007 | A | 7/1996 | St. Germain et al. |
| 5,569,199 | A | 10/1996 | Solar |
| 5,571,087 | A | 11/1996 | Ressemann et al. |
| 5,591,197 | A | 1/1997 | Orth et al. |
| 5,667,521 | A | 9/1997 | Keown |
| 5,669,880 | A | 9/1997 | Solar |
| 5,681,346 | A | 10/1997 | Orth et al. |
| 5,685,847 | A | 11/1997 | Barry |
| 5,749,825 | A | 5/1998 | Fischell et al. |
| 5,769,821 | A | 6/1998 | Abrahamson et al. |
| 5,772,594 | A | 6/1998 | Barrick |
| 5,830,227 | A | 11/1998 | Fischell et al. |
| 5,980,484 | A | 11/1999 | Ressemann et al. |
| 5,992,000 | A | 11/1999 | Humphrey et al. |
| 6,007,517 | A | 12/1999 | Anderson |
| 6,048,361 | A | 4/2000 | Von Oepen |
| 6,068,610 | A | 5/2000 | Ellis et al. |
| 6,082,990 | A | 7/2000 | Jackson et al. |
| 6,110,097 | A | 8/2000 | Hastings et al. |
| 6,165,195 | A | 12/2000 | Wilson et al. |
| 6,210,431 | B1 | 4/2001 | Power |
| 6,273,879 | B1 | 8/2001 | Keith et al. |
| 6,375,660 | B1 | 4/2002 | Fischell et al. |
| 6,394,995 | B1 * | 5/2002 | Solar et al. .................. 604/528 |
| 6,428,567 | B2 | 8/2002 | Wilson et al. |
| 6,440,097 | B1 | 8/2002 | Kupiecki |
| 6,440,161 | B1 | 8/2002 | Madrid et al. |
| 6,458,151 | B1 | 10/2002 | Saltiel |
| 6,508,836 | B2 | 1/2003 | Wilson et al. |
| 6,520,988 | B1 | 2/2003 | Colombo et al. |
| 6,544,218 | B1 | 4/2003 | Choi |
| 6,562,064 | B1 | 5/2003 | deBeer |
| 6,579,312 | B2 | 6/2003 | Wilson et al. |
| 6,582,394 | B1 | 6/2003 | Reiss et al. |
| 6,676,691 | B1 | 1/2004 | Hosny |
| 6,676,702 | B2 | 1/2004 | Mathis |
| 6,682,556 | B1 | 1/2004 | Ischinger |
| 6,692,460 | B1 | 2/2004 | Jayaraman |
| 6,692,483 | B2 | 2/2004 | Vardi et al. |
| 6,733,487 | B2 | 5/2004 | Keith et al. |
| 6,740,104 | B1 * | 5/2004 | Solar et al. .................. 606/194 |
| 6,780,199 | B2 | 8/2004 | Solar et al. |
| 7,300,415 | B2 * | 11/2007 | McMurtry et al. ......... 604/96.01 |
| 7,314,480 | B2 * | 1/2008 | Eidenschink et al. ....... 623/1.11 |
| 7,344,557 | B2 | 3/2008 | Yadin |
| 7,399,307 | B2 | 7/2008 | Evans et al. |
| 7,455,688 | B2 | 11/2008 | Furst et al. |
| 7,655,030 | B2 | 2/2010 | Williams et al. |
| 7,753,951 | B2 | 7/2010 | Shaked et al. |
| 7,766,951 | B2 | 8/2010 | Shaked |
| 7,780,715 | B2 | 8/2010 | Shaked et al. |
| 7,901,378 | B2 | 3/2011 | Solar et al. |
| 8,070,729 | B2 | 12/2011 | Solar et al. |
| 8,262,621 | B2 | 9/2012 | Solar et al. |
| 2001/0004706 | A1 | 6/2001 | Hojeibane |
| 2001/0012927 | A1 | 8/2001 | Mauch |
| 2001/0016767 | A1 | 8/2001 | Wilson et al. |
| 2001/0016768 | A1 | 8/2001 | Wilson et al. |
| 2001/0029396 | A1 | 10/2001 | Wilson et al. |
| 2001/0037116 | A1 | 11/2001 | Wilson et al. |
| 2001/0037138 | A1 | 11/2001 | Wilson et al. |
| 2001/0049548 | A1 | 12/2001 | Vardi et al. |
| 2001/0056297 | A1 | 12/2001 | Hojeibane |
| 2002/0022874 | A1 | 2/2002 | Wilson |
| 2002/0077692 | A1 | 6/2002 | Besselink |
| 2002/0091434 | A1 | 7/2002 | Chambers |
| 2002/0111675 | A1 | 8/2002 | Wilson |
| 2002/0138128 | A1 | 9/2002 | Stiger et al. |
| 2002/0147491 | A1 | 10/2002 | Khan et al. |
| 2002/0177869 | A1 | 11/2002 | Eidenschink et al. |
| 2003/0009209 | A1 | 1/2003 | Hojeibane |
| 2003/0028233 | A1 | 2/2003 | Vardi et al. |
| 2003/0028235 | A1 | 2/2003 | McIntosh et al. |
| 2003/0050688 | A1 | 3/2003 | Fischell et al. |
| 2003/0055398 | A1 | 3/2003 | Imran |
| 2003/0055483 | A1 | 3/2003 | Gumm |
| 2003/0074046 | A1 | 4/2003 | Richter |
| 2003/0074047 | A1 | 4/2003 | Richter |
| 2003/0114912 | A1 | 6/2003 | Sequin et al. |
| 2003/0114920 | A1 | 6/2003 | Caro et al. |
| 2003/0125761 | A1 * | 7/2003 | Meens et al. .................. 606/192 |
| 2003/0135259 | A1 | 7/2003 | Simso |
| 2003/0167083 | A1 | 9/2003 | Lashinski et al. |
| 2003/0171642 | A1 | 9/2003 | Schock et al. |
| 2003/0181923 | A1 | 9/2003 | Vardi |
| 2003/0187494 | A1 | 10/2003 | Loaldi |
| 2003/0191436 | A1 * | 10/2003 | Horvers .................. 604/103.04 |
| 2004/0098087 | A1 | 5/2004 | Madrid et al. |
| 2004/0111143 | A1 | 6/2004 | Fischell et al. |
| 2004/0122465 | A1 | 6/2004 | McMurtry et al. |
| 2004/0138734 | A1 | 7/2004 | Chobotov et al. |
| 2004/0172121 | A1 * | 9/2004 | Eidenschink et al. ....... 623/1.11 |
| 2004/0220511 | A1 | 11/2004 | Scott et al. |
| 2005/0015135 | A1 | 1/2005 | Shanley |
| 2005/0084130 | A1 | 4/2005 | Yamagishi |
| 2005/0101968 | A1 | 5/2005 | Dadourian |
| 2005/0137196 | A1 | 6/2005 | Timmer et al. |
| 2005/0154440 | A1 | 7/2005 | Limon |
| 2005/0209673 | A1 | 9/2005 | Shaked |
| 2005/0209677 | A1 | 9/2005 | Shaked |
| 2005/0267508 | A1 | 12/2005 | Kato et al. |
| 2006/0106448 | A1 | 5/2006 | Shaked |
| 2006/0111689 | A1 | 5/2006 | Rosenschein et al. |
| 2006/0271090 | A1 | 11/2006 | Shaked et al. |
| 2007/0173918 | A1 | 7/2007 | Dreher et al. |
| 2007/0244431 | A1 | 10/2007 | Limon |
| 2008/0033525 | A1 | 2/2008 | Shaked et al. |
| 2008/0082050 | A1 | 4/2008 | Solar et al. |
| 2008/0228146 | A1 | 9/2008 | Shaked et al. |
| 2009/0275920 | A1 | 11/2009 | Solar et al. |
| 2010/0234800 | A1 | 9/2010 | Shaked |
| 2010/0241212 | A1 | 9/2010 | Shaked et al. |
| 2010/0286720 | A1 | 11/2010 | Shaked et al. |
| 2011/0118774 | A1 | 5/2011 | Solar et al. |
| 2011/0190708 | A1 | 8/2011 | Shaked et al. |

FOREIGN PATENT DOCUMENTS

| | | |
|---|---|---|
| EP | 1931344 A2 | 10/2009 |
| EP | 2430990 A1 | 3/2012 |
| JP | 2012055719 A | 3/2012 |
| JP | 5032566 B2 | 7/2012 |
| JP | 5137568 | 11/2012 |
| WO | 9117714 | 11/1991 |
| WO | 9526777 A1 | 10/1995 |
| WO | 9808727 A1 | 3/1998 |
| WO | 2010074273 A1 | 10/2001 |
| WO | 0239926 A2 | 5/2002 |
| WO | 02067653 A2 | 9/2002 |
| WO | 02067815 A1 | 9/2002 |
| WO | 02067816 A1 | 9/2002 |
| WO | 03051234 A1 | 6/2003 |
| WO | 03061529 A1 | 7/2003 |
| WO | 03063729 A2 | 8/2003 |
| WO | 03068307 A1 | 8/2003 |
| WO | 2004008994 A1 | 1/2004 |
| WO | 2004103216 A1 | 12/2004 |
| WO | 2005084130 A2 | 9/2005 |
| WO | 2007039902 A3 | 4/2009 |
| WO | 2007132447 A3 | 4/2009 |

OTHER PUBLICATIONS

EP 05709151.4 filed Mar. 3, 2005 Office Action dated Jul. 8, 2010.
EP 05709151.4 filed Mar. 3, 2005 Search Report dated Jul. 10, 2009.
EP 06796143.3 filed Oct. 3, 2006 Office Action dated Jan. 21, 2011.
EP 06796143.3 filed Oct. 3, 2006 Office Action dated Jan. 7, 2010.
EP 06796143.3 filed Oct. 3, 2006 Search Report dated Sep. 29, 2009.
EP 07736308.3 filed May 10, 2007 Office Action dated Jan. 13, 2010.

EP 07736308.3 filed May 10, 2007 Office Action dated Jan. 20, 2011.
EP 07736308.3 filed May 10, 2007 Search Report dated Nov. 11, 2009.
JP 2007501448 filed Mar. 3, 2005 Office Action dated Jun. 21, 2010.
PCT/IL2005/000258 filed Mar. 3, 2005 International Preliminary Report on Patentability dated Sep. 5, 2006.
PCT/IL2005/000258 filed Mar. 3, 2005 Search Report dated Jan. 3, 2006.
PCT/IL2005/000258 filed Mar. 3, 2005 Written Opinion dated Jan. 3, 2006.
PCT/IL2006/001150 filed Oct. 3, 2006 International Preliminary Report on Patentability dated Mar. 10, 2009.
PCT/IL2006/001150 filed Oct. 3, 2006 Search Report dated Jul. 11, 2008.
PCT/IL2006/001150 filed Oct. 3, 2006 Written Opinion dated Jun. 22, 2008.
PCT/IL2007/000568 filed May 10, 2007 International Preliminary Report on Patentability dated Mar. 31, 2009.
PCT/IL2007/000568 filed May 10, 2007 Search Report dated Oct. 3, 2008.
PCT/IL2007/000568 filed May 10, 2007 Written Opinion dated Apr. 9, 2008.
U.S. Appl. No. 11/240,631 filed Oct. 3, 2005 Final Office Action dated Dec. 16, 2009.
U.S. Appl. No. 11/240,631 filed Oct. 3, 2005 Non-Final Office Action dated Jun. 15, 2009.
U.S. Appl. No. 11/240,631 filed Oct. 3, 2005 Notice of Allowance dated Feb. 26, 2010.
U.S. Appl. No. 11/240,631 filed Oct. 3, 2005 Notice of Allowance dated Jun. 3, 2010.
U.S. Appl. No. 11/431,918 filed May 11, 2006 Advisory Action dated Feb. 25, 2010.
U.S. Appl. No. 11/431,918 filed May 11, 2006 Final Office Action dated Dec. 16, 2009.
U.S. Appl. No. 11/431,918 filed May 11, 2006 Non-Final Office Action dated Jun. 16, 2009.
U.S. Appl. No. 11/431,918 filed May 11, 2006 Notice of Allowance dated Apr. 14, 2010.
U.S. Appl. No. 11/685,228 filed Mar. 13, 2007 Final Office Action dated Mar. 5, 2010.
U.S. Appl. No. 11/685,228 filed Mar. 13, 2007 Final Office Action dated Nov. 29, 2010.
U.S. Appl. No. 11/685,228 filed Mar. 13, 2007 Non-Final Office Action dated May 13, 2009.
U.S. Appl. No. 11/746,682 filed May 10, 2007 Notice of Allowance dated Sep. 29, 2010.
U.S. Appl. No. 11/868,568 filed Oct. 8, 2007 Notice of Allowance dated Mar. 2, 2010.
U.S. Appl. No. 12/503,119 filed Jul. 15, 2009 Non-Final Office Action dated Jun. 9, 2010.
U.S. Appl. No. 12/503,119 filed Jul. 15, 2009 Notice of Allowance dated Dec. 28, 2010.
CN 2007800157415.5 Certificate of Patent for Invention dated Oct. 3, 2012.
CN 2007800157415.5 Office Action dated Feb. 6, 2012.
CN 2007800157415.5 Office Action dated Sep. 15, 2011.
EP 05709151.4 filed Mar. 3, 2005 Office Action dated Jan. 17, 2012.
EP 06796143.3 filed Oct. 3, 2006 Examination Report dated Apr. 4, 2012.
EP 06796143.3 filed Oct. 3, 2006 Office Action dated Nov. 9, 2011.
EP 07736308.3 filed May 10, 2007 Office Action dated Aug. 30, 2011.
EP 07736308.3 filed May 10, 2007 Office Action dated Jan. 26, 2012.
EP 11193221.6 filed Oct. 3, 2006 European Search Report dated Feb. 14, 2012.
JP 2008-532975 filed Oct. 3, 2006 Official Action dated Sep. 15, 2011.
JP 2009-508666 filed Oct. 31, 2008 Office Action dated Feb. 1, 2012.
U.S. Appl. No. 11/746,682, filed May 10, 2007 Final Rejection dated Apr. 27, 2010.
U.S. Appl. No. 11/746,682, filed May 10, 2007 Non-Final Rejection dated Aug. 24, 2009.
U.S. Appl. No. 12/787,067, filed May 25, 2010 Non-Final Office Action dated Aug. 27, 2012.
U.S. Appl. No. 12/791,787, filed Jun. 1, 2010 Non-Final Office Action dated Jul. 19, 2012.
U.S. Appl. No. 12/838,286, filed Jul. 16, 2010 Final Office Action dated Nov. 8, 2012.
U.S. Appl. No. 12/838,286, filed Jul. 16, 2010 Non-Final Office Action dated May 23, 2012.
U.S. Appl. No. 13/009,767, filed Jan. 19, 2011 Non-Final Office Action dated Oct. 5, 2011.
U.S. Appl. No. 13/009,767, filed Jan. 19, 2011 Notice of Allowance dated May 24, 2012.
U.S. Appl. No. 12/787,067, filed May 25, 2010 Advisory Action dated Mar. 22, 2013.
U.S. Appl. No. 12/787,067, filed May 25, 2010 Final Office Action dated Jan. 16, 2013.
U.S. Appl. No. 12/791,787, filed Jun. 1, 2010 Final Office Action dated Jan. 30, 2013.
U.S. Appl. No. 12/838,286, filed Jul. 16, 2010 Non-Final Office Action dated Jan. 25, 2013.
U.S. Appl. No. 13/035,670, filed Feb. 25, 2011 Non-Final Office Action dated Mar. 4, 2013.

* cited by examiner

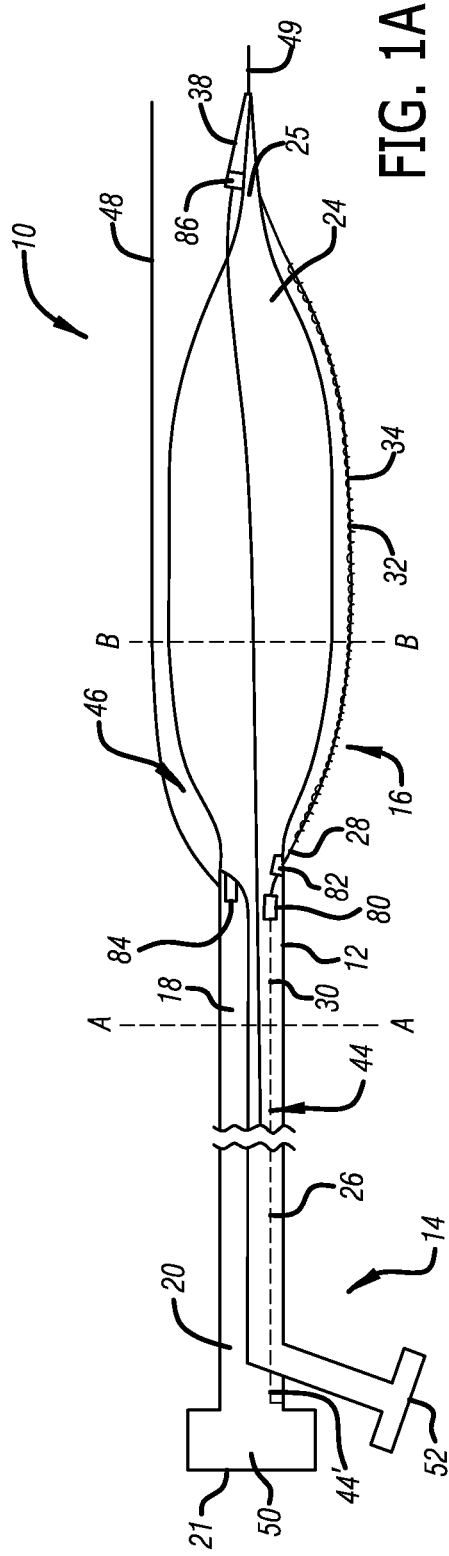

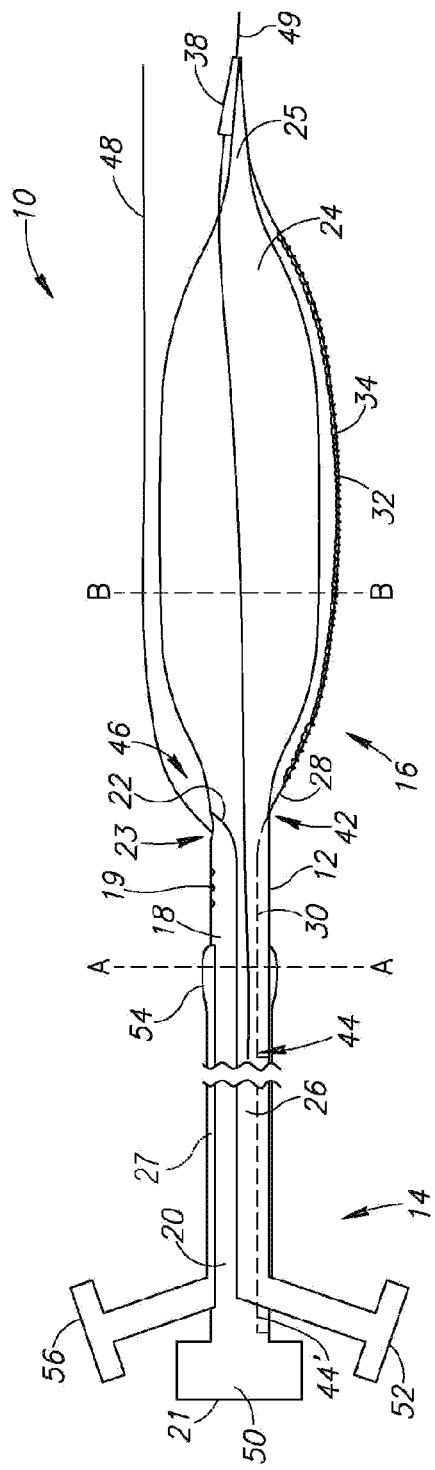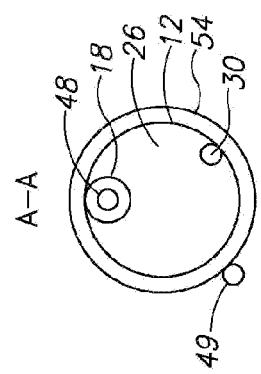
FIG.1F
FIG.1G

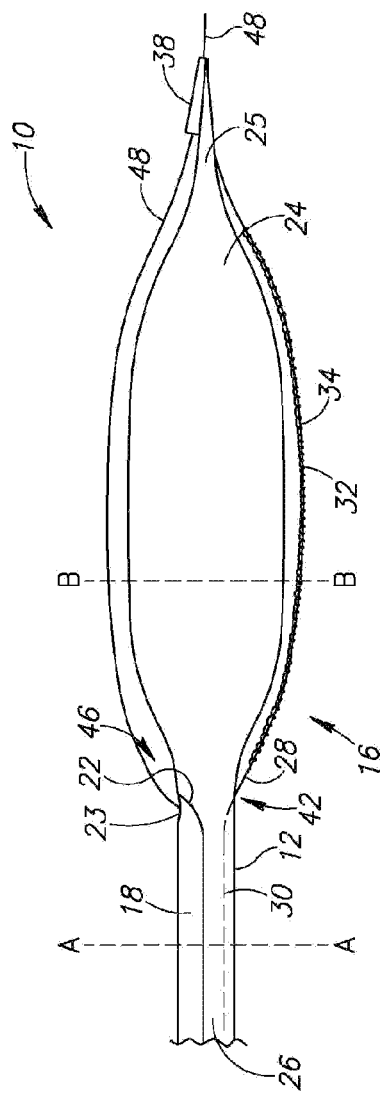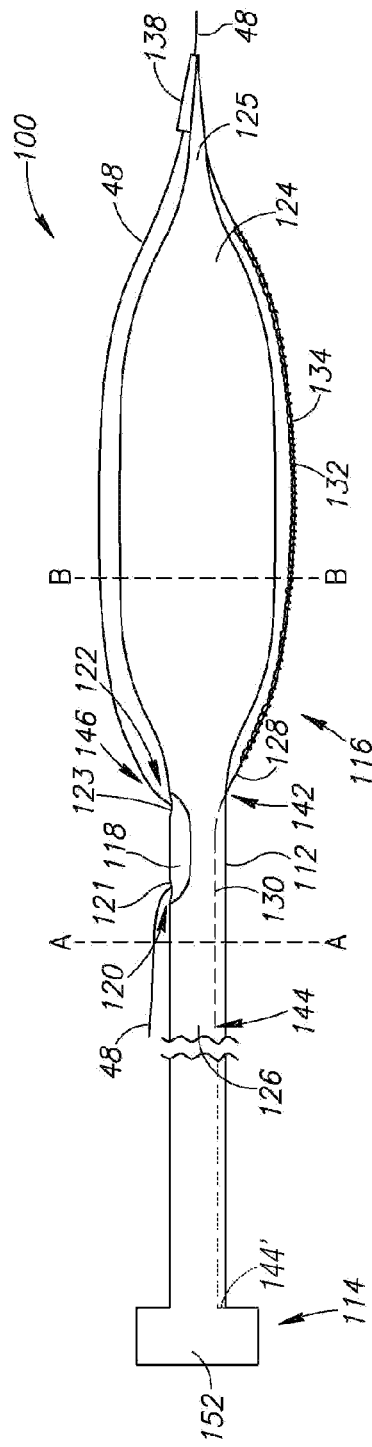

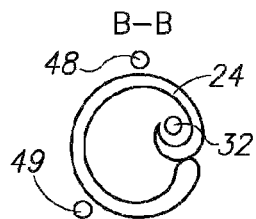
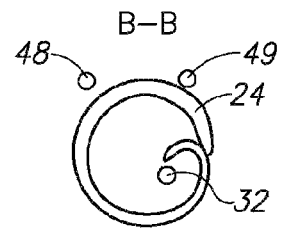
FIG.6A                    FIG.6B
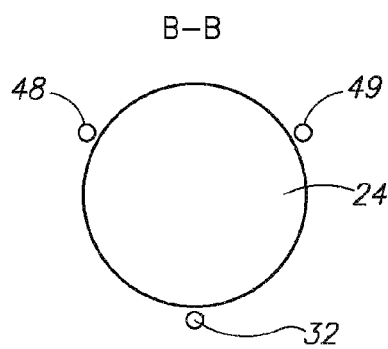
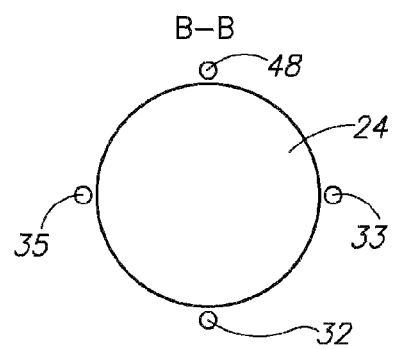
FIG.6C                    FIG.6D

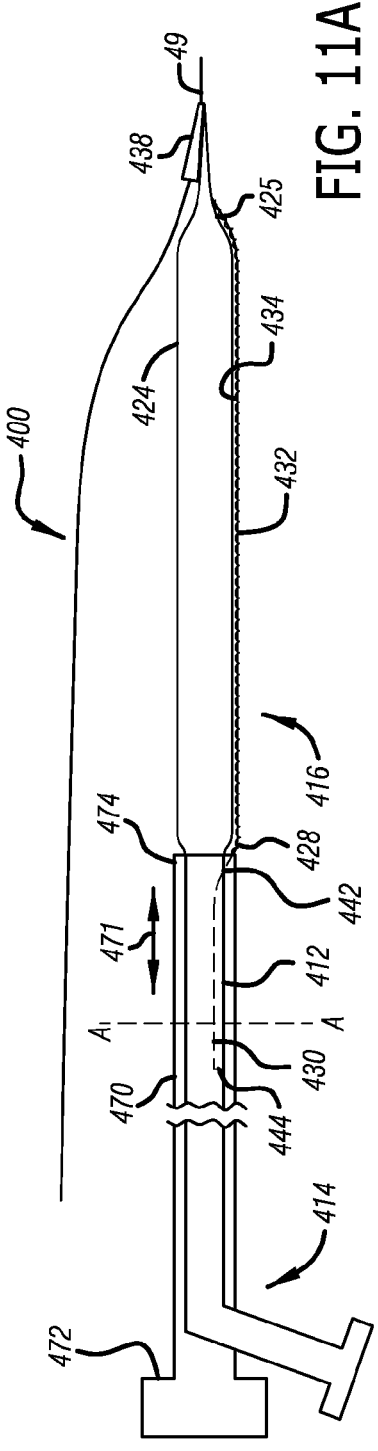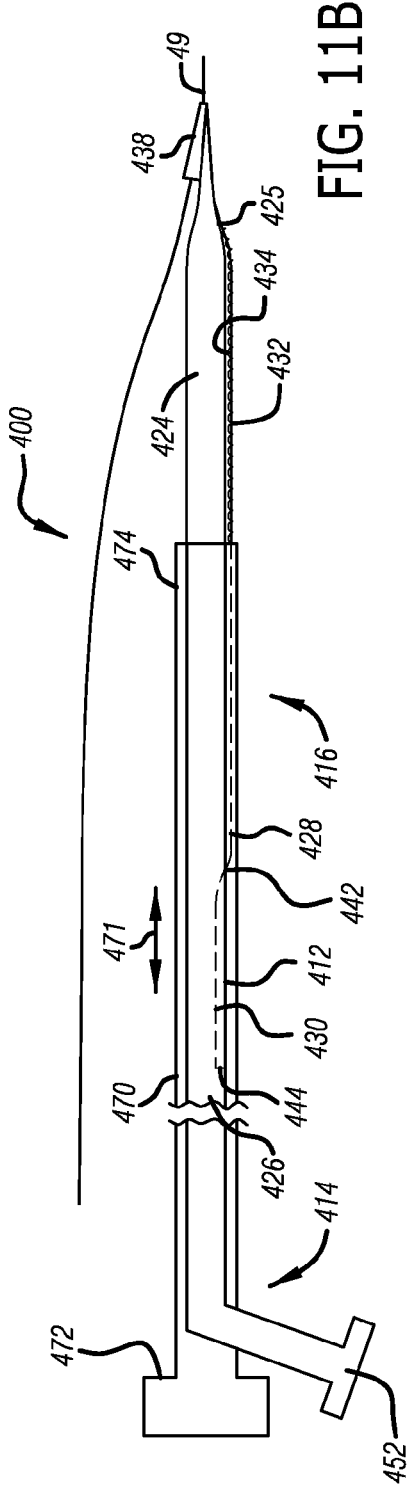

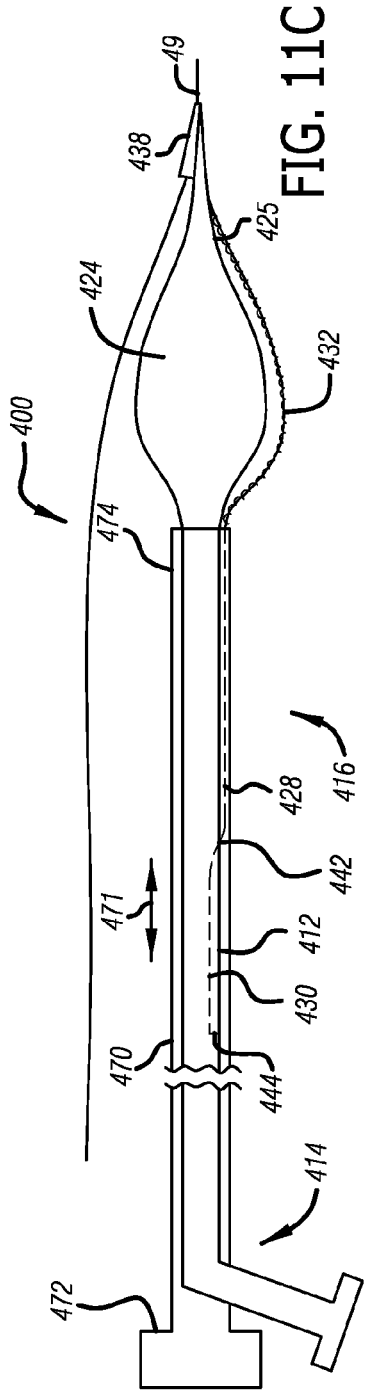
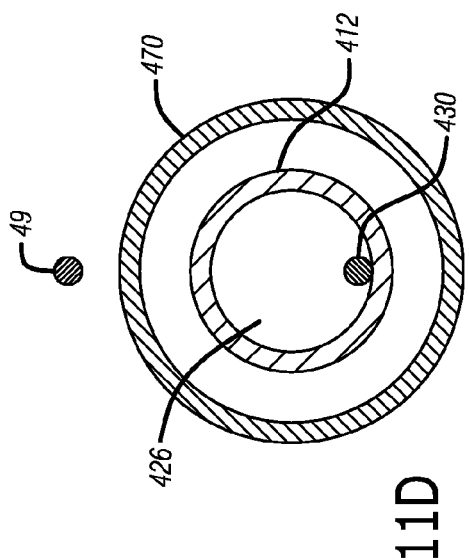
FIG. 11C
FIG. 11D

SYSTEMS AND METHODS FOR TREATING A VESSEL USING FOCUSED FORCE

CROSS REFERENCES TO RELATED APPLICATIONS

This application is a continuation-in-part of U.S. patent application Ser. No. 11/746,682, filed May 10, 2007, now U.S. Pat. No. 7,901,378, which is a continuation-in-part of U.S. patent application Ser. No. 11/431,918, filed May 11, 2006, now U.S. Pat. No. 7,780,715, and a continuation-in-part of International Patent Application No. PCT/IL2006/001150, filed Oct. 3, 2006, each of which aforementioned applications is incorporated by reference in its entirety into this application.

FIELD OF THE INVENTION

The present invention relates to a rapid exchange balloon catheter system having an adjustable balloon length.

BACKGROUND OF THE INVENTION

Balloon dilatation catheters are used to treat lesions in vessels. However, difficulties are encountered in navigating tortuous anatomy and safely crossing very tight lesions. Moreover, some lesions are longer in length than others, and oftentimes multiple lesions need to be treated in a single patient. Thus, it would be beneficial to have a balloon catheter system having rapid exchange capabilities wherein a length of the balloon could be adjusted during the procedure and used to treat multiple lesions of varying lengths. Known balloon dilation catheters provide limited focused force, do not address bifurcation lesions, and lack pushability and maneuverability.

SUMMARY OF THE INVENTION

Embodiments of a device for introduction into a vessel are generally described including a main elongated element having a main elongated element proximal end and a main elongated element distal end, a balloon positioned at the main elongated element distal end, the balloon having a balloon proximal end, a balloon distal end, and an inflation lumen therethrough, a distal connecting element positioned at the distal end of the balloon to receive a guidewire during use, and a longitudinally movable sheath positioned external to the main elongated element, the longitudinally movable sheath having a distal end and a proximal end, wherein a position of the sheath distal end with respect to the balloon defines an exposed portion of the balloon that expands when fluid is delivered to the balloon through the inflation lumen.

The sheath of the device may include a tapered end to provide a reduced diameter entry profile for the device. When initially introduced into the vessel, the sheath may be at a distal position covering the balloon to provide a reduced diameter tip where only the distal connecting element is exposed for introduction over a guidewire. The distal end of the sheath may also include a tapered end with a soft edge that expands upon retraction of the sheath over the balloon. The body of the sheath may include a braided or helically wrapped coil to prevent an unexposed portion of the balloon from expanding when the sheath is positioned external to the unexposed portion of the balloon. The sheath may also include a polymeric liner or outer jacket in order to provide additional strength.

Embodiments as described herein may further include a core wire unslidingly attached to said main elongated element at a core wire attachment point including an internal core wire portion positioned within said main elongated element and an external core wire portion positioned distally with respect to said internal core wire portion, said external core wire portion external to and running alongside said balloon. The external core wire portion may further include a coil wrapped around at least a portion thereof, where the coil-wrapped portion is positioned adjacent to the balloon.

The device may also include one or more radiopaque markers to indicate the position of the device within the vessel and a rotational orientation. Accordingly, a first and second radiopaque marker may be longitudinally aligned, such as on the described core while, while a third radiopaque marker is positioned off the longitudinal axis, such as on an auxiliary elongate element or the distal connecting element.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The above and further advantages of the present invention may be better understood by referring to the following description in conjunction with the accompanying drawings in which:

FIG. 1A is a schematic illustration of a system for treatment of a vessel, in accordance with embodiments of the present invention;

FIGS. 1B-1D are cross-sectional illustrations of the system of FIG. 1A;

FIG. 1F is a schematic illustration of the system of FIG. 1A, with an occlusion balloon;

FIG. 1G is a cross-sectional illustration of the system of FIG. 1F;

FIG. 2 is a schematic illustration of a system for treatment of a vessel, in accordance with other embodiments of the present invention;

FIG. 3 is a schematic illustration of a system for treatment of a vessel, in accordance with yet additional embodiments of the present invention;

FIGS. 6A-6D are cross-sectional illustrations of a distal portion of the systems of FIGS. 1-4;

FIGS. 11A-11D are schematic illustrations of a system in accordance with additional embodiments of the present invention, wherein a sheath is positioned over a main elongated element;

Figure 1E:
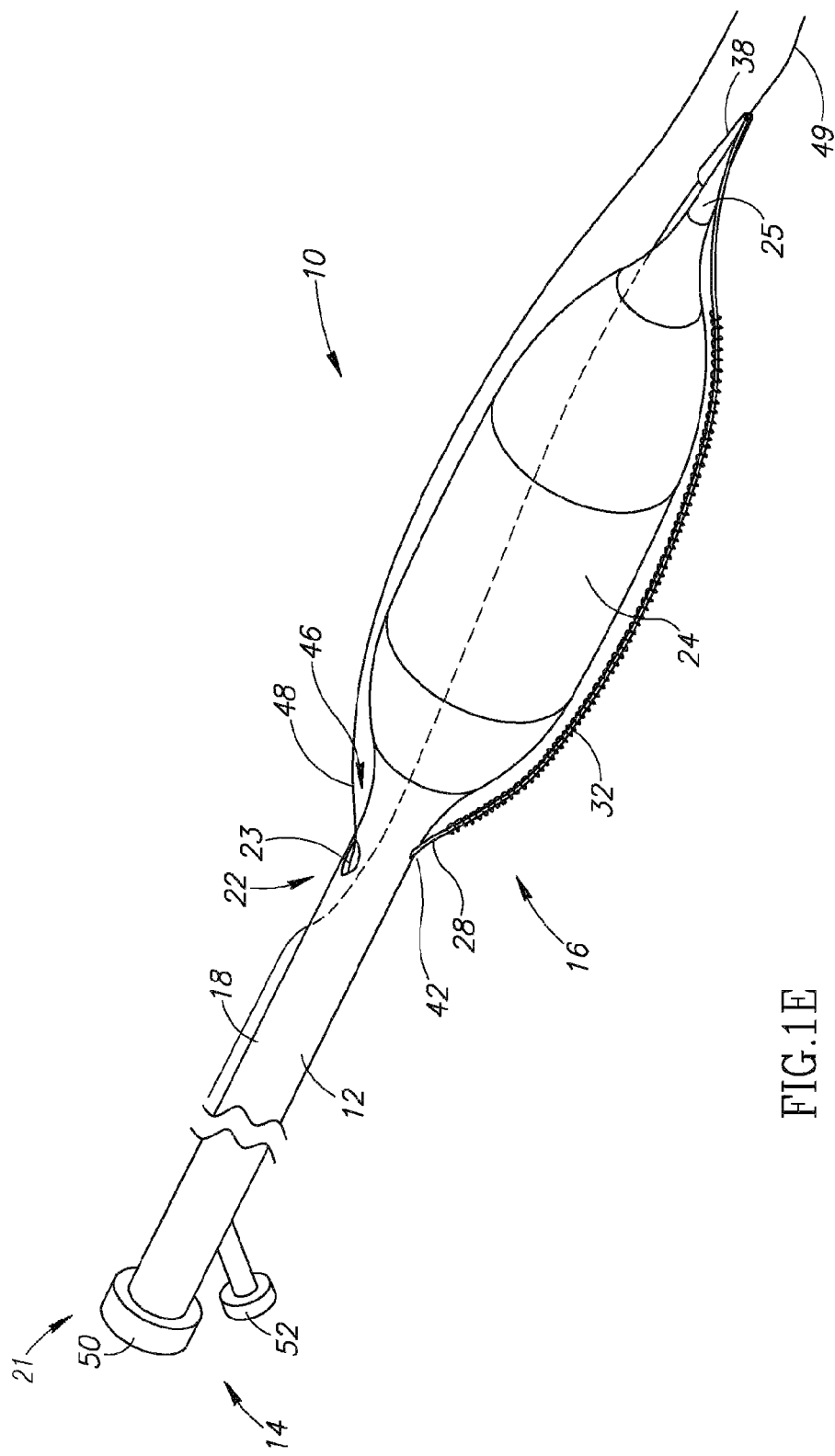
FIG. 1E is a perspective illustration of the system of FIG. 1A.

It will be appreciated that for simplicity and clarity of illustration, elements shown in the drawings have not necessarily been drawn accurately or to scale. For example, the dimensions of some of the elements may be exaggerated relative to other elements for clarity or several physical components may be included in one functional block or element. Further, where considered appropriate, reference numerals may be repeated among the drawings to indicate corresponding or analogous elements. Moreover, some of the blocks depicted in the drawings may be combined into a single function.

DETAILED DESCRIPTION

In the following detailed description, numerous specific details are set forth in order to provide a thorough understanding of the present invention. It will be understood by those of ordinary skill in the art that the present invention may be practiced without these specific details. In other instances, well-known methods, procedures, components and structures may not have been described in detail so as not to obscure the present invention.

The present invention is directed to systems and methods for treatment of a vessel including an adjustable balloon length. The principles and operation of a system and methods according to the present invention may be better understood with reference to the drawings and accompanying descriptions.

Before explaining at least one embodiment of the present invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein are for the purpose of description and should not be regarded as limiting.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Reference is now made to FIGS. 1A and 1E, which are a schematic and perspective illustration, respectively, of a system 10 for treatment of a vessel, in accordance with embodiments of the present invention. System 10 includes a main elongated element 12 having a proximal end 14 and a distal end 16. In some embodiments of the present invention, main elongated element 12 is a catheter shaft. A balloon 24 is positioned at distal end 16 of main elongated element 12. Balloon 24 can be comprised of a variety of diameters, ranging from 1.25-10.0 mm, for example, and a variety of lengths, ranging from 10 mm to 30 cm, for example. Long balloons may be particularly useful for treating peripheral lesions, which often have long diseased portions. System 10 further includes an auxiliary elongated element 18 configured to receive a guidewire 48 therethrough. Auxiliary elongated element 18 has a proximal end 20 with a proximal exit point 21 for guidewire 48 and a distal end 22 with a distal exit point 23 for guidewire 48. In some embodiments, at least a portion of auxiliary elongated element 18 is positioned within main elongated element 12 so as to reduce the outer profile of system 10. Distal end 22 of auxiliary elongated element 18 is proximal to balloon 24 such that guidewire 48, when positioned through auxiliary elongated element 18, exits distal exit point 23 and runs alongside and external to balloon 24. This configuration provides for a focused force element alongside balloon 24, as will be described further hereinbelow. In some embodiments, such as the one shown in FIGS. 1A and 1E, auxiliary elongated element 18 runs along the length of main elongated element 12 to a proximal guidewire port 50. This configuration provides an over-the-wire type of configuration. In this embodiment, auxiliary elongated element 18 may be used for items other than a guidewire, such a drug delivery, sensors, or to hold a mandrel therein so as to provide additional rigidity to the system when needed. In the embodiment wherein guidewire 48 is used, guidewire 48 positioned through distal exit point 23 forms a crotch point 46 at or near a proximal end of balloon 24. The presence of a crotch point may be useful, for example, for anchoring system 10 within a side branch to avoid slippage within the vessel to be treated, or to provide for precise positioning of system 10 at a bifurcation.

In some embodiments, main elongated element 12 is stiffer proximally than distally. This may be accomplished, for example, by using a metal hypotube in the proximal portion and a polymer or other flexible material in the distal portion. This configuration provides more flexibility at the distal end to allow for easier maneuverability through tortuous vessels, while maintaining rigidity at a proximal end for pushability. However, if the distal portion of main elongated element 12 is too flexible, it will be difficult to push through the vessels. Thus, system 10 further includes a core wire 28, which provides enhanced pushability of system 10 without significantly reducing the flexibility of system 10. Core wire 28 is provided in the flexible portion, and may terminate at the stiff portion when no longer needed for rigidity. In other embodiments, main elongated element 12 is relatively flexible along all or most of its length, by using a flexible polymer or other flexible material to form main elongated element 12. In these embodiments, core wire 28 may run along an entire length of main elongated element 12 and may vary in diameter along the length so as to provide increased rigidity at proximal end 14. In some embodiments, the flexible shaft may also be braided or otherwise strengthened to provide sufficient rigidity.

In embodiments of the present invention, core wire 28 has a portion positioned within main elongated element 12, referred to herein as internal core wire portion 30, and a portion positioned external to main elongated element 12, referred to herein as external core wire portion 32. Internal core wire portion 30 is proximal to external core wire portion 32, and is attached to main elongated element 12 at an internal core wire attachment point 44. As discussed further below with respect to FIG. 5A, external core wire portion 32 may be configured with a coil 34. For embodiments wherein main elongated element 12 is comprised of a relatively flexible distal portion and a relatively rigid proximal portion, internal core wire attachment point 44 is located at an interface between the stiff proximal portion and the flexible distal portion, for example, a distal end of the hypotube. In embodiments wherein main elongated element is mostly or completely comprised of flexible material, internal core wire attachment point 44' is located at proximal end 14 of system 10. However, it should be readily apparent that internal core wire attachment point 44 may be located at any location along the length of main elongated element 12. Moreover, multiple internal core wire attachment points 44 may be included. At a location proximal to balloon 24, internal core wire portion 30 exits main elongated element 12 and becomes external core wire portion 32. This location is referred to herein as a core wire exit point 42. In one embodiment, core wire exit point 42 is at a distal end of main elongated element 12. In other embodiments, core wire exit point 42 is at other locations along main elongated element 12 (but in most cases proximal to balloon 24). Distal to core wire exit point 42, external core wire portion 32 is positioned alongside balloon 24, and a distal end of external core wire portion 32 is attached to a distal tip 25 of balloon 24. Several attachment or bonding locations provide transmission of forces through the length of the catheter, and thus enhance overall torquability and rotatability. In particular, bonding can be done at any or all of the following locations: at distal tip 25 of balloon 24, at core wire exit point 42, and at internal core wire attachment point 44. Additional attachment points may be included as well. It should be noted that the use of an internal core wire makes it possible to have a longer flexible (polymeric or other) portion or even a completely flexible shaft, enhancing overall flexibility of system 10.

In some embodiments, a triangular marker configuration is used to rotationally orient the system 10. Rotational orientation may be necessary, for example, when re-entering a guidewire into a vessel after entry into or creation of a subintimal lumen during treatment. Other instances requiring rotational orientation may occur as well. As such, a marker configuration which can aid in rotational positioning of system 10 would be beneficial. As shown in FIG. 1A, a first radiopaque marker 80 and a second radiopaque marker 82 are positioned on a section of core wire 28, and a third radiopaque marker 84 is positioned on auxiliary elongated element 18 at distal exit point 23. As described above, core wire 28 may be attached at multiple points along main elongated element 12, which is important both for general rigidity and for stability and maintained alignment of first and second radiopaque markers 80 and 82. In one rotational position, markers 80 and 82 are approximately aligned along a longitudinal axis, while marker 84 is on a different longitudinal axis than markers 80 and 82. If system 10 is rotated 90 degrees from the first position, all three markers 80, 82 and 84 are roughly aligned. Thus, by viewing the relative positions of markers 80, 82 and 84, it is possible to determine a rotational orientation of system 10 and as such, a rotational position of guidewire 48. A constant longitudinal distance between markers 80, 82 and 84 may be maintained to clearly mark the rotational relationships between the markers.

System 10 further includes a distal connecting element 38 at distal tip 25 of balloon 24. Distal connecting element 38 may be a short rail, ranging in length from 2-20 mm, or may be a longer rail, ranging in length from 1-4 cm, and more specifically in a range of approximately 2.5 cm. A longer distal connecting element 38 may provide additional support for crossing tight or chronic occlusions. Distal connecting element 38 may be bonded to distal tip 25 such that the proximal end of distal connecting element 38 is distal to balloon 24. In the case of a longer rail, distal connecting element 38 may then extend distally past balloon 24. A radiopaque marker 86 may be included on distal connecting element 38. This may be particularly useful in case guidewire 48 slips out of distal connecting element 38 and must be guided back in. A three-way bond may be used to attach distal connecting element 38, balloon 24 and external core wire portion 32, all together. Distal connecting element 38 may be tapered toward its distal end to facilitate passage through tight stenoses. Distal connecting element 38 is positioned at a rotational distance from auxiliary elongated element 18 and from external core wire portion 32, and is configured to hold a tracking guidewire 49 therethrough. In some embodiments, distal connecting element 38, auxiliary elongated element 18 and external core wire portion 32 are positioned approximately 120° from one another. In other embodiments, other rotational distances may be used, such that there is some rotational separation between them. In this way, guidewire 48, tracking guidewire 49 and core wire 32 may all lie alongside balloon 24 at different rotational positions along balloon 24 when balloon 24 is in its expanded state. Although the separations between guidewire 48, tracking guidewire 49 and core wire 32 are not required to be any specific amounts, it should be apparent that the distances between them should be sufficient to provide separate wires alongside several different areas of balloon 24. Each of these wires can then provide a focused force to help crack difficult lesions, as will be explained further hereinbelow. It should be noted that in some embodiments, guidewire 48 and tracking guidewire 49 may be of different sizes.

Reference is now made to FIGS. 1B-1D, which are cross-sectional illustrations of system 10 shown at section A-A, in accordance with several embodiments of the present invention. As shown in FIG. 1B, an interior portion of main elongated element 12 serves as an inflation lumen 26, providing fluid communication between an inflation port 52 located at proximal end 14 of main elongated element 12 and balloon 24 located at distal end 16 of main elongated element 12. In some embodiments, a portion of the interior of main elongated element 12 is sectioned off for use as inflation lumen 26, as shown in FIG. 1C and in FIG. 1D, wherein only the sectioned off inflation lumen 26 is in fluid communication with inflation port 52. Auxiliary elongated element 18 is positioned within main elongated element along an edge thereof. The cross-sectional views of FIGS. 1B-1D show auxiliary elongated element 18 with guidewire 48 positioned therein. Internal core wire portion 30 is positioned within main elongated element 12. In some embodiments, as shown in FIGS. 1B and 1C, internal core wire portion 30 is positioned along an edge of main elongated element 12. In other embodiments, as shown in FIG. 1D, internal core wire portion 30 is positioned in a center of main elongated element 12. It should be readily apparent, however, that at core wire attachment point 44 and at core wire exit point 42, the core wire is in contact with or close proximity to an edge of main elongated element 12. Tracking guidewire 49 is shown external to main elongated element 12.

Reference is now made to FIGS. 1F and 1G, which are schematic and cross-sectional illustrations of system 10 further including an occlusion balloon 54. Occlusion balloon 54 is positioned around main elongated element 12 and is proximal to auxiliary element distal exit point 23. As shown in FIG. 1F, an inflation lumen 27 provides fluid communication between an inflation port 56 located at proximal end 14 of main elongated element 12 and occlusion balloon 54 located along the main elongated element 12. Occlusion balloon 54 may be used to temporarily occlude blood flow proximal to occlusion balloon 54, and to enable introduction of an item or a substance into the vessel at the lesion site via auxiliary elongated element 18. In some embodiments, the item is a treatment device, such as a guidewire with an ablation tip or any other treatment device. In some embodiments, the substance is contrast media. In other embodiments, the substance is a therapeutic drug or medicated solution. In some embodiments, multiple ports 19 may be included on auxiliary elongated element 18, distal to occlusion balloon 54. These multiple ports 19 may enable spraying of a substance such as contrast media, drugs, medicated solutions, etc.

Reference is now made to FIG. 2, which is a schematic illustration of system 10, wherein distal connecting element 38 is aligned with auxiliary elongated element 18, such that guidewire 48 may be positioned through distal connecting element 38 and further through auxiliary elongated element 18, and out through auxiliary elongated element proximal exit point 21. Thus, only one guidewire is used in the configuration shown in FIG. 2. This design provides a single guidewire enclosure split into two sections—one at the distal end and one at the proximal end of balloon 24—in order to reduce the profile of system 10 in the vicinity of balloon 24 during introduction of system 10 into a vessel. Guidewire 48, while positioned within distal connecting element 38 and auxiliary elongated element 18, can serve as a focused force to help crack difficult lesions and may also be used as a tracking guidewire for advancing system 10 into the vessel.

Reference is now made to FIG. 3, which is a schematic illustration of a system 100, in accordance with additional embodiments of the present invention. System 100 includes a main elongated element 112 having a proximal end 114 and a distal end 116. In some embodiments of the present invention, main elongated element 112 is a catheter shaft. A balloon 124 is positioned at distal end 116 of main elongated element 112. An interior portion of main elongated element 112 serves as an inflation lumen 126, providing fluid communication between an inflation port 152 located at proximal end 114 of main elongated element 112 and balloon 124 located at distal end 116 of main elongated element 112. Balloon 124 can be comprised of a variety of diameters, ranging from 1.25-10.0 mm, for example, and a variety of lengths, ranging from 10 mm to 30 cm, for example. Long balloons may be particularly useful for treating peripheral lesions, which often have long diseased portions. System 100 further includes an auxiliary elongated element 118 configured to receive a guidewire 48 therethrough. Auxiliary elongated element 118 has a proximal end 120 with a proximal exit point 121 for guidewire 48 and a distal end 122 with a distal exit point 123 for guidewire 48. In some embodiments, at least a portion of auxiliary elongated element 118 is positioned within main elongated element 112 so as to reduce the outer profile of system 100. Distal end 122 of auxiliary elongated element 118 is proximal to balloon 124 such that guidewire 48, when positioned through auxiliary elongated element 118, exits distal exit point 123 and runs alongside and external to balloon 124. This configuration provides for a focused force element alongside balloon 124, as will be described further hereinbelow. In some embodiments, such as the one shown in FIG. 3, auxiliary elongated element 118 is relatively short, extending 5-30 cm, and in some embodiments approximately 20 cm. This configuration enables rapid exchange in cases when system 100 may need to be retracted and a different device reinserted over guidewire 48. In some embodiments, auxiliary elongated element 118 is a solid piece rather than a lumen, and is used for enhanced bonding of a core wire 128, as will be described hereinbelow. In one embodiment, guidewire 48 positioned through distal exit point 123 forms a crotch point 146 at or near a proximal end of balloon 124. The presence of a crotch point may be useful, for example, for anchoring system 100 within a side branch to avoid slippage within the vessel to be treated, or to provide for precise positioning of system 100 at a bifurcation.

In some embodiments, main elongated element 112 is stiffer proximally than distally. This may be accomplished, for example, by using a metal hypotube in the proximal portion and a polymer or other flexible material in the distal portion. This configuration provides more flexibility at the distal end to allow for easier maneuverability through tortuous vessels, while maintaining rigidity at a proximal end for pushability. However, if the distal portion of main elongated element 112 is too flexible, it will be difficult to push through the vessels. Thus, system 100 further includes a core wire 128, which provides enhanced pushability of system 100 without significantly reducing the flexibility of system 100. Core wire 128 is provided in the flexible portion, and may terminate at the stiff portion when no longer needed for rigidity. In other embodiments, main elongated element 112 is relatively flexible along all or most of its length, by using a flexible polymer or other flexible material to form main elongated element 112. In these embodiments, core wire 128 may run along an entire length of main elongated element 112 and may vary in diameter along the length so as to provide increased rigidity at proximal end 114. In some embodiments, the flexible shaft may also be braided or otherwise strengthened to provide sufficient rigidity.

In embodiments of the present invention, core wire 128 has a portion positioned within main elongated element 112, referred to herein as internal core wire 130, and a portion positioned external to main elongated element 112, referred to herein as external core wire 132. For embodiments wherein main elongated element 112 is comprised of a relatively flexible distal portion and a relatively rigid proximal portion, internal core wire attachment point 144 is located at an interface between the stiff proximal portion and the flexible distal portion, for example, a distal end of the hypotube. In embodiments wherein main elongated element is mostly or completely comprised of flexible material, internal core wire attachment point 144' is located at proximal end 114 of system 100. However, it should be readily apparent that internal core wire attachment point 144 may be located at any location along the length of main elongated element 112. Moreover, multiple internal core wire attachment points 144 may be included. At a location proximal to balloon 124, internal core wire 130 exits main elongated element 112 and becomes external core wire 132. This location is referred to herein as a core wire exit point 142. In one embodiment, core wire exit point 142 is at a distal end of main elongated element 112 (but in most cases proximal to balloon 124). In other embodiments, core wire exit point 142 is at other locations along main elongated element 112. Distal to core wire exit point 142, external core wire 132 is positioned alongside balloon 124, and a distal end of external core wire 132 is attached to a distal tip 125 of balloon 124. Several attachment or bonding locations provide transmission of forces through the length of the catheter, and thus enhance overall torquability and rotatability. In particular, bonding can be done at any or all of the following locations: at a distal tip 125 of balloon 124, at core wire exit point 142, and at internal core wire attachment point 144. Additional attachment points may be included as well. Bonding may be done by bonding auxiliary elongated element 118, and core wire 128 together. It should be noted that the use of an internal core wire makes it possible to have a longer flexible (polymeric or other) portion or even a completely flexible shaft, enhancing overall flexibility of system 100. As described further with respect to FIG. 5A, external core wire portion 132 may be configured with a coil 134.

System 100 further includes a distal connecting element 138 at distal tip 125 of balloon 124. Distal connecting element 138 may be a short rail, ranging in length from 2-20 mm, or may be a longer rail, ranging in length from 1-4 cm, and more specifically in a range of approximately 2.5 cm. A longer distal connecting element 138 may provide additional support for crossing tight or chronic occlusions. Distal connecting element 138 may be bonded to distal tip 125 such that the proximal end of distal connecting element 138 is distal to balloon 124. In the case of a longer rail distal connecting element 138 may then extend distally past balloon 124. A radiopaque marker may be included on distal connecting element 138. This may be particularly useful in case guidewire 48 slips out of distal connecting element 138 and must be guided back in. A three-way bond may be used to attach distal connecting element 138, balloon 124 and core wire 132 all together. Distal connecting element 138 may be tapered toward its distal end to facilitate passage through tight stenoses. Distal connecting element 138 is aligned with auxiliary elongated element 118, such that guidewire 48 may be positioned through distal connecting element 138 and further through auxiliary elongated element 118, and out through auxiliary elongated element proximal exit point 121. Thus, only one guidewire is used in the configuration shown in FIG. 3. This design provides a single guidewire enclosure split into two sections—one at the distal end and one at the proximal end of balloon 124—in order to reduce the profile of system 100 in the vicinity of balloon 124 during introduction of system 100 into a vessel. Guidewire 48, while positioned within distal connecting element 138 and auxiliary elongated element 118, can serve as a focused force to help crack difficult lesions and may also be used as a tracking guidewire for advancing system 100 into the vessel.

Figure 4:
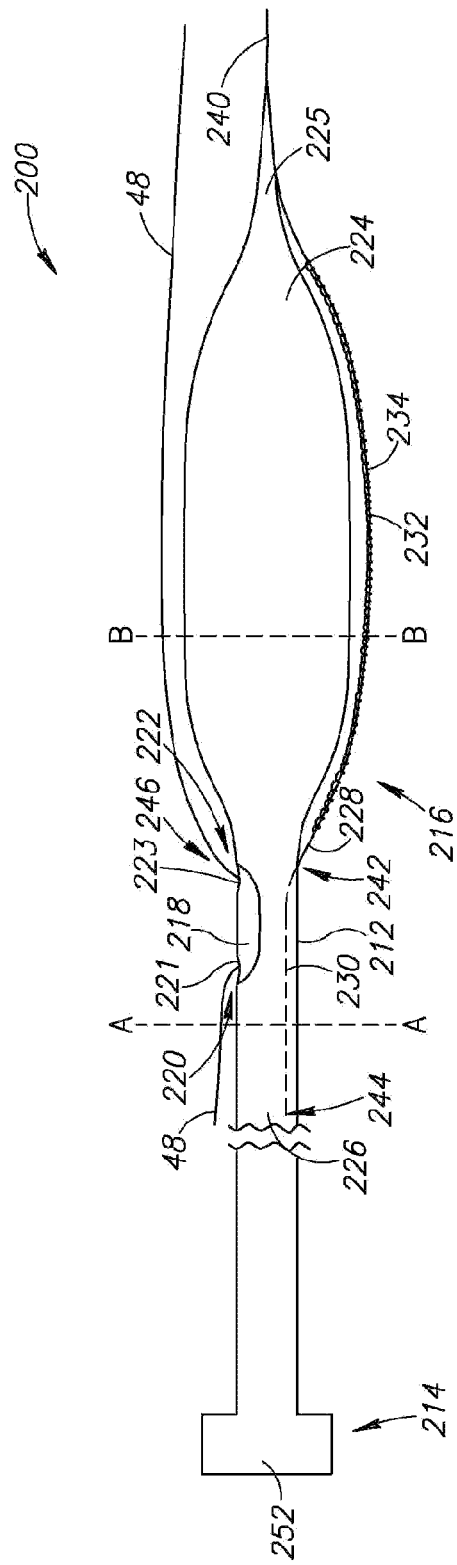
FIG. 4 is a schematic illustration of a system for treatment of a vessel, in accordance with yet additional embodiments of the present invention.

Reference is now made to FIG. 4, which is a schematic illustration of a system 200 for treatment of a vessel, in accordance with yet additional embodiments of the present invention. The embodiment shown in FIG. 4 has a reduced profile due to the use of a fixed wire balloon, and may be particularly useful for smaller peripheral vessels such as infra-popliteal vessels, for example. System 200 includes a main elongated element 212 having a proximal end 214 and a distal end 216. In some embodiments of the present invention, main elongated element 212 is a catheter shaft. A balloon 224 is positioned at distal end 216 of main elongated element 212. An interior portion of main elongated element 212 serves as an inflation lumen 226, providing fluid communication between an inflation port 252 located at proximal end 214 of main elongated element 212 and balloon 224 located at distal end 216 of main elongated element 212. Balloon 224 can be comprised of a variety of diameters, ranging from 1.25-10.0 mm, for example, and a variety of lengths, ranging from 10 mm to 30 cm, for example. Long balloons may be particularly useful for treating peripheral lesions, which often have long diseased portions. In the embodiment depicted in FIG. 4, balloon 224 is a fixed wire balloon. In one embodiment, balloon 224 is a fixed wire balloon as is commonly known in the art. An example of such a balloon is the type used for the Ace™ Balloon Catheter of Boston Scientific Corporation (Natick, Mass., USA). In another embodiment, balloon 224 is any balloon with a fixed wire 240 attached thereto. System 200 further includes an auxiliary elongated element 218 configured to receive a guidewire 48 therethrough. Auxiliary elongated element 218 has a proximal end 220 with a proximal exit point 221 for guidewire 48 and a distal end 222 with a distal exit point 223 for guidewire 48. In some embodiments, at least a portion of auxiliary elongated element 218 is positioned within main elongated element 212 so as to reduce the outer profile of system 200. Distal end 222 of auxiliary elongated element 218 is proximal to balloon 224 such that guidewire 48, when positioned through auxiliary elongated element 218, exits distal exit point 223 and runs alongside and external to balloon 224. This configuration provides for a focused force element alongside balloon 224, as will be described further hereinbelow. In some embodiments, such as the one shown in FIG. 4, auxiliary elongated element 218 is relatively short, extending 5-30 cm, and in some embodiments approximately 20 cm. This configuration enables rapid exchange in cases when system 200 may need to be retracted and a different device reinserted over guidewire 48. In other embodiments, auxiliary elongated element 218 may continue proximally along the entire length of main elongated element 212 for an over-the-wire configuration, such as described above with reference to FIG. 1A. In one embodiment, guidewire 48 positioned through distal exit point 223 forms a crotch point 246 at or near a proximal end of balloon 224. The presence of a crotch point may be useful, for example, for anchoring system 200 within a side branch to avoid slippage within the vessel to be treated, or to provide for precise positioning of system 100 at a bifurcation.

In some embodiments, main elongated element 212 is stiffer proximally than distally. This may be accomplished, for example, by using a metal hypotube in the proximal portion and a polymer or other flexible material in the distal portion. This configuration provides more flexibility at the distal end to allow for easier maneuverability through tortuous vessels, while maintaining rigidity at a proximal end for pushability. However, if the distal portion of main elongated element 212 is too flexible, it will be difficult to push through the vessels. Thus, system 200 further includes a core wire 228, which provides enhanced pushability of system 200 without significantly reducing the flexibility of system 200. Core wire 228 is provided in the flexible portion, and may terminate at the stiff portion when no longer needed for rigidity. In other embodiments, main elongated element 212 is relatively flexible along all or most of its length, by using a flexible polymer or other flexible material to form main elongated element 212. In these embodiments, core wire 228 may run along an entire length of main elongated element 212 and may vary in diameter along the length so as to provide increased rigidity at proximal end 214. In some embodiments, the flexible shaft may also be braided or otherwise strengthened to provide sufficient rigidity.

In embodiments of the present invention, core wire 228 has a portion positioned within main elongated element 212, referred to herein as internal core wire 230, and a portion positioned external to main elongated element 212, referred to herein as external core wire 232. As discussed further below with respect to FIG. 5A, external core wire portion 232 may be configured with a coil 234. For embodiments wherein main elongated element 212 is comprised of a relatively flexible distal portion and a relatively rigid proximal portion, internal core wire attachment point 244 is located at an interface between the stiff proximal portion and the flexible distal portion, for example, a distal end of the hypotube. In embodiments wherein main elongated element is mostly or completely comprised of flexible material, internal core wire attachment point 244 is located at proximal end 214 of system 200. However, it should be readily apparent that internal core wire attachment point may be located at any location along the length of main elongated element 212. Moreover, multiple internal core wire attachment points 244 may be included. At a location proximal to balloon 224, internal core wire 230 exits main elongated element 212 and becomes external core wire 232. This location is referred to herein as a core wire exit point 242. In one embodiment, core wire exit point 242 is at a distal end of main elongated element 212 (but in most cases proximal to balloon 224). In other embodiments, core wire exit point 242 is at other locations along main elongated element 212. Distal to core wire exit point 242, external core wire 232 is positioned alongside balloon 224, and a distal end of external core wire 232 is attached to a distal tip 225 of balloon 224. Several attachment or bonding locations provide transmission of forces through the length of the catheter, and thus enhance overall torquability and rotatability. In particular, bonding can be done at any or all of the following locations: at a distal tip of balloon 224, at core wire exit point 242, and at internal core wire attachment point 244. Additional attachment points may be included as well. It should be noted that the use of an internal core wire makes it possible to have a longer flexible (polymeric or other) portion or even a completely flexible shaft, enhancing overall flexibility of system 200. In some embodiments, external core wire 232 and fixed wire 240 are comprised of the same wire. In other embodiments, some or all of external core wire 232 and fixed wire 240 are separate pieces of wire which are connected at the distal tip 225 of balloon 224.

In all of the systems described above, a hydrophilic coating may be added externally to provide ease of insertion.

Figure 5A:
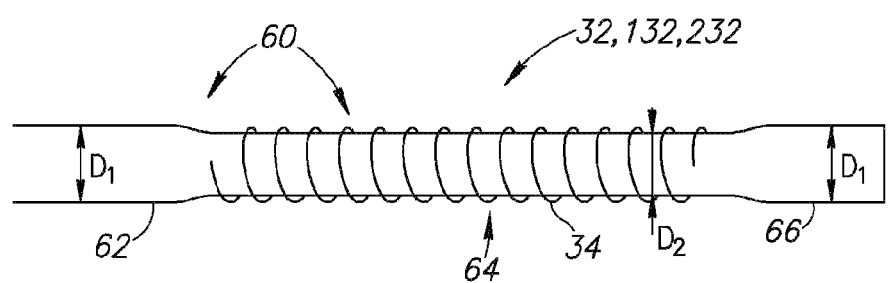
FIGS. 5A and 5B are illustrations of a core wire, in accordance with embodiments of the present invention.
Figure 5B:
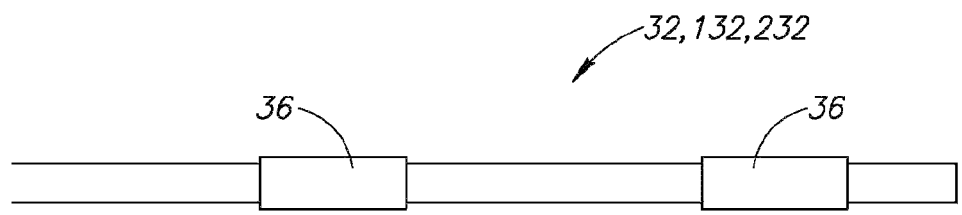

Reference is now made to FIG. 5A and FIG. 5B, which are schematic illustrations of external core wire portion 32, 132, 232 in accordance with embodiments of the present invention. As shown in FIG. 5A, external core wire portion 32, 132 or 232 is configured with a wire portion 60 and a coil 34. Wire portion 60 includes a proximal wire section 62, a mid-wire section 64 and a distal wire section 66. Proximal and distal wire sections 62 and 66 both have a diameter D1 which is greater than a diameter D2 of mid-wire section 64. Coil 34 is wrapped around mid-wire section 64. When in position on system 10, 100, 200, mid-wire section 64 with coil 34 runs alongside balloon 24, 124, 224. This configuration provides enhanced flexibility as well as gripping at the lesion so that slippage of balloon 24, 124, 224 against the lesion is reduced. Moreover, in some embodiments, coil 34 is comprised of radiopaque material, and thus acts as a marker for positioning of system 10, 100 or 200.

Reference is now made to FIG. 5B, which is an illustration of external core wire portion 32, 132, 232 in accordance with another embodiment of the present invention. Core wire 32, 132, 232 may be a wire having at least one radiopaque marker 36 thereon. Multiple markers 36 may be used, and may be spaced at optimal locations such as at a proximal end and a distal end of balloon 24, for example.

Although external core wire portion 32 is positioned external to balloon 24 when balloon 24 is in its inflated state, as shown in FIGS. 1A, 2, 3 and 4, when balloon 24 is in its deflated state (i.e., during insertion of system 10 into the body), external core wire portion 32 may be positioned within folds of balloon 24. Reference is now made to FIG. 6A-6D, which are cross-sectional illustrations along line B-B of system 10 showing external core wire portion 32, guidewire 48, tracking guidewire 49, and balloon 24 in its deflated state (FIGS. 6A and 6B) and its inflated state (FIGS. 6C and 6D). It should be readily apparent that similar configurations are possible for systems 100 and 200 as well. As shown in FIGS. 6A and 6B, when balloon 24 is in its deflated configuration, external core wire portion 32 is positioned within folds of balloon 24. If a guidewire 48 and/or tracking guidewire 49 are present, guidewire 48 and tracking guidewire 49 can be seen alongside balloon 24. As shown in FIG. 6C, when balloon 24 is expanded, external core wire portion 32 is positioned alongside balloon 24. The external position of external core wire portion 32 with respect to balloon 24 provides an area of focused force for cracking or breaking up hard or difficult lesions. Guidewire 48 and tracking guidewire 49 may be used to provide an additional area of focused force. In some embodiments, guidewire 48 is positioned at a rotational distance from external core wire portion 32 so as to provide multiple areas of focused force around system 10. For example, auxiliary elongated element 18 may be positioned approximately 180 degrees from external core wire portion 32, or approximately 120 degrees from external core wire portion 32 and approximately 120 degrees from tracking guidewire 49, although it should be readily apparent that many different rotational distances are possible.

Reference is now made to FIG. 6D, which is a cross-sectional illustration along line B-B, in accordance with another embodiment. In this embodiment, additional external core wires 33 and 35 are present as well. Although shown with three external core wires, any suitable number of core wires may be used. In one embodiment, core wire 28 is split into multiple wires at core wire exit point 42, and the multiple core wires are bundled together at distal end 16 of system 10. In an alternative embodiment, multiple core wire exit points 42 are spaced around main elongated element 12, and multiple core wires exit through the multiple core wire exit points. They are then bundled together at distal tip 25 of balloon 24.

Figure 7A:
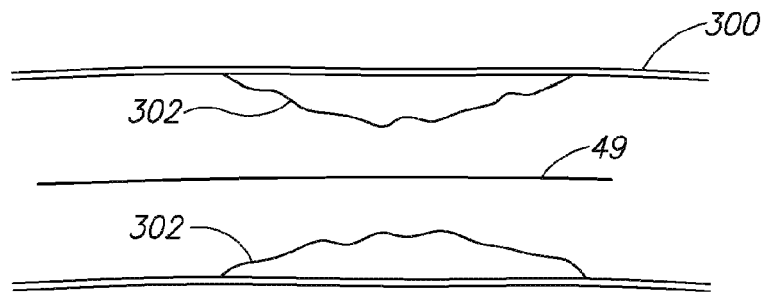
FIGS. 7A-7F are schematic illustrations of the steps of a method of treating a vessel, in accordance with embodiments of the present invention.
Figure 7B:
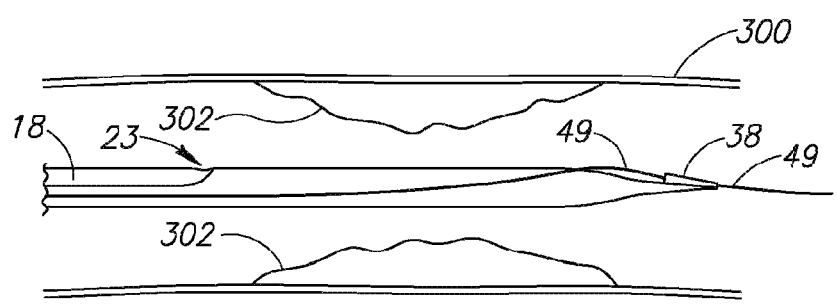
Figure 7C:
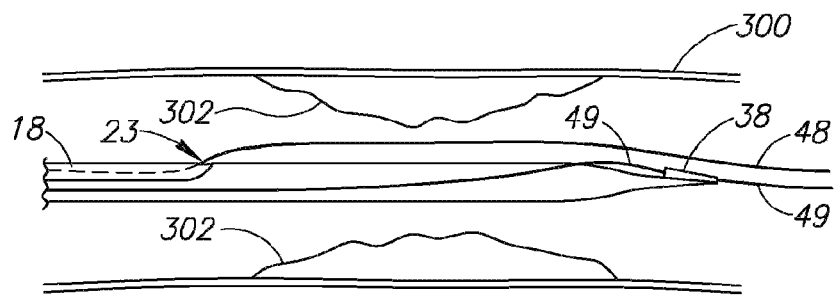
Figure 7D:
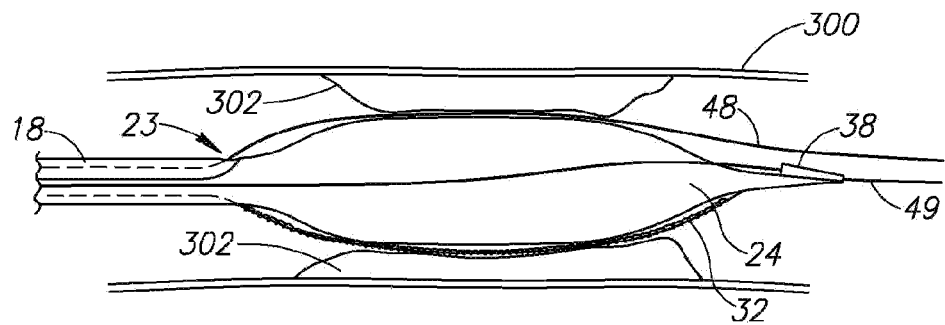

Reference is now made to FIGS. 7A-7E, which are schematic illustrations of the steps of a method of treating a vessel, in accordance with embodiments of the present invention. A vessel 300 having a lesion 302 is accessed via tracking guidewire 49 as shown in FIG. 7A. Tracking guidewire 49 is backloaded onto system 10 by placing tracking guidewire 49 through distal connecting element 38, and system 10 is advanced over tracking guidewire 49 to the vicinity of lesion 302, as shown in FIG. 7B. Next, an additional guidewire 48 may be positioned through auxiliary elongated element 18, and advanced until a distal end of guidewire 48 is distal to balloon 24, as shown in FIG. 7C. In some instances, when guidewire 48 is difficult to advance to this distal location, system 10 may be advanced distally past lesion 302, such that distal exit point 23 of auxiliary elongated element 18 is beyond lesion 302. Guidewire 48 is then advanced through auxiliary elongated element 18. System 10 may then be pulled back proximally so that guidewire 48 and tracking guidewire 49 are adjacent balloon 24 and are in a vicinity of lesion 302. Balloon 24 is then expanded, as shown in FIG. 7D. Expansion of balloon 24 causes external core wire portion 32 to be released from within folds of balloon 24. Expansion of balloon 24 further causes guidewire 48, tracking guidewire 49 and external core wire portion 32 to be pushed up against lesion 302 in three separate rotational positions around the vessel and the lesion. The presence of guidewire 48, tracking guidewire 49, and/or external core wire portion 32 provides a focused force to enable the user to crack hard lesions at low pressure before balloon 24 is fully inflated. Doing so allows vessel stretching to occur at a lower strain rate, thus minimizing the trauma associated with balloon dilatation.

Figure 7E:
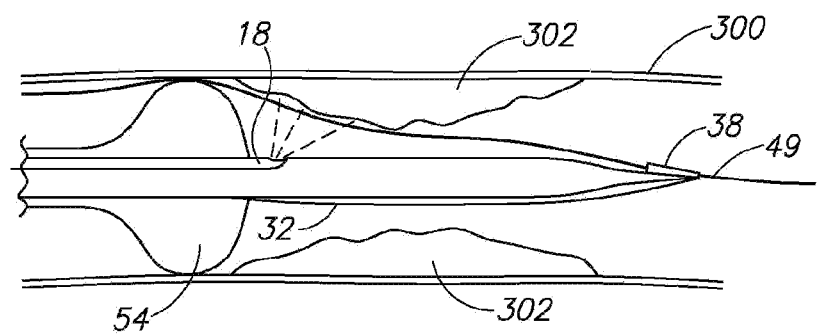
Figure 7F:
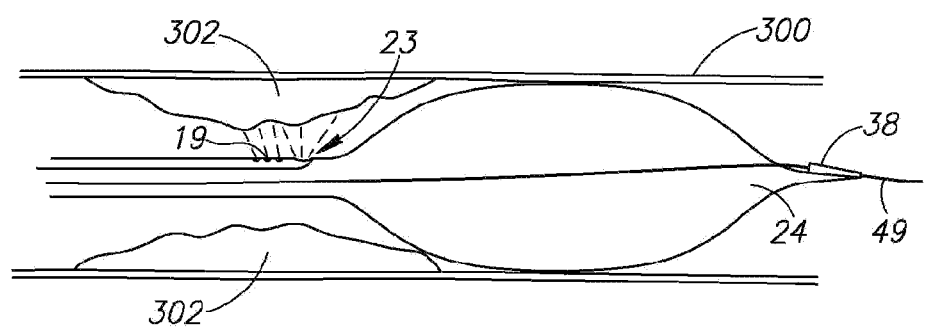

In some embodiments, auxiliary elongated lumen 18 may further be used to provide an item or substance to the vessel. Reference is now made to FIG. 7E, which is a schematic illustration of system 10 positioned inside vessel 300. After the lesion has been cracked or pushed open via balloon 24 and/or external core wire portion 32 and/or guidewire 48, and/or tracking guidewire 49, balloon 24 may then be deflated. In some embodiments, guidewire 48 is retracted to provide an open lumen for delivery of an object or drug to vessel 300. Occlusion balloon 54 is inflated, blocking the portion of vessel 300 which is proximal to occlusion balloon 54. Then, a drug, contrast media or other treatment device may be inserted through auxiliary elongated element 18 and used to treat vessel 300. In some embodiments, after deflating balloon 24, system 10 is advanced past the lesion, occlusion balloon 54 is inflated and treatment is provided to a portion of vessel 300 which is distal to lesion 302. In yet another embodiment, as shown in FIG. 1A, system 10 does not have occlusion balloon 54. After deflating balloon 24, system 10 is advanced past the lesion. Balloon 24 is reinflated at low pressure to occlude vessel 300, and treatment is provided to a portion of vessel 300 that is distal to lesion 302. In some embodiments, ports 19 may provide additional access for treatment of the vessel by spraying treatment solution, for example.

In some embodiments, auxiliary elongated element 18 may be used to introduce a "buddy wire" for tortuous vessels. The "buddy wire" concept is known in the art, and involves introducing a secondary wire alongside a catheter to help straighten out curved vessels and ease the way for the catheter. However, by using a system such as the ones described herein, the "buddy wire" may be introduced within the catheter, minimizing the risk of puncture of the vessel or entanglement of the buddy wire with the catheter. Moreover, systems of the present invention may also be used to introduce a second wire for bifurcations, wherein guidewire 48 introduced through auxiliary elongated element 18 and tracking guidewire 49 may both remain in the vessel. When the system is removed from the body, guidewire 48 is prevented from entanglement with tracking guidewire 49 since guidewire 48 is positioned within auxiliary elongated element 18. Thus, any crossing over which may occur is automatically straightened out during removal of system 10. An additional use of system 10 is in cases where a practitioner encounters a "false lumen". That is, if tracking guidewire 49 encounters an area which is not a true lumen, an additional guidewire 48 may be introduced through system 10 and through the true lumen. System 10 may then be retracted proximally, and advanced over guidewire 48 to cross the lesion.

Figure 8A:
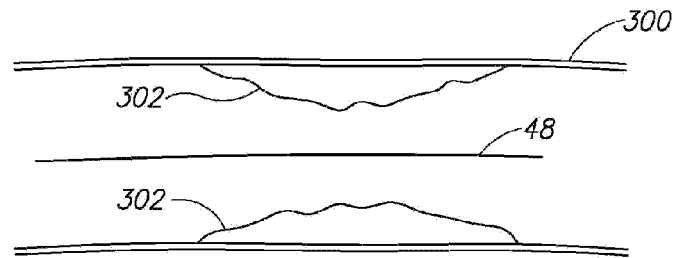
FIGS. 8A-8C are schematic illustrations of the steps of a method of treating a vessel, in accordance with additional embodiments of the present invention.
Figure 8B:
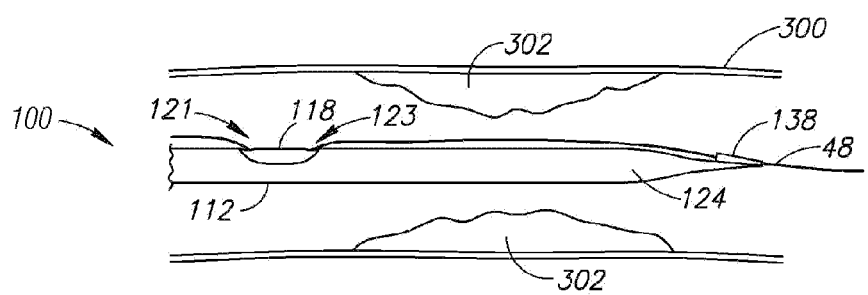
Figure 8C:
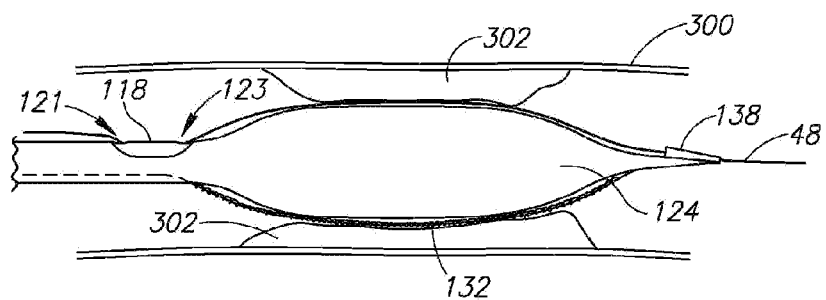

Reference is now made to FIGS. 8A-8C, which are schematic illustrations of the steps of a method of treating a vessel, in accordance with embodiments of the present invention. A vessel 300 having a lesion 302 is accessed via guidewire 48, as shown in FIG. 8A. Guidewire 48 is backloaded onto system 100 by placing guidewire 48 through distal connecting element 138, and further positioning guidewire 48 through auxiliary elongated element 118, as shown in FIG. 8B. In some embodiments, an introducer is used to help place guidewire 48 into distal exit point of auxiliary elongated element 118. The introducer may be, for example, a mandrel having a female end, which is pre-loaded into both auxiliary elongated element 118 and distal connecting element 138. When guidewire 48 is backloaded into distal connecting element 138, the proximal end of guidewire 48 is positioned within the female end of the mandrel. The mandrel may then be pulled back proximally, leading guidewire 48 into auxiliary elongated element 118. Guidewire 48 is thus positioned through both distal connecting element 138 and through auxiliary elongated element 118, and exits through auxiliary elongated element proximal exit point 121, which may be relatively close to auxiliary elongated element distal exit point 123 for rapid exchange as shown in FIG. 8B, or may be at the proximal end of main elongated element 112 for an over-the-wire configuration. System 100 is advanced over guidewire 48, and positioned such that balloon 124 is adjacent lesion 302, as shown in FIG. 8B. It should be noted that external core wire 132 is not shown in FIG. 8B during insertion, since it is folded into balloon 124. Balloon 124 is then inflated, which pushes both guidewire 48 and external core wire 132 up against lesion 302. The presence of guidewire 48 and/or external core wire 132 provides a focused force to enable the user to crack hard lesions at low pressure before balloon 124 is fully inflated. Doing so allows vessel stretching to occur at a lower strain rate, thus minimizing the trauma associated with balloon dilatation.

Figure 9A:
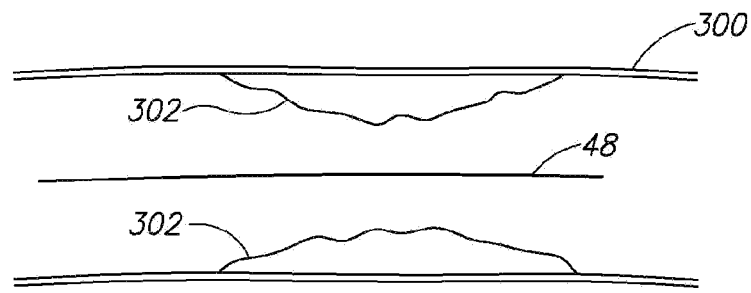
FIGS. 9A-9C are schematic illustrations of the steps of a method of treating a vessel, in accordance with additional embodiments of the present invention.
Figure 9B:
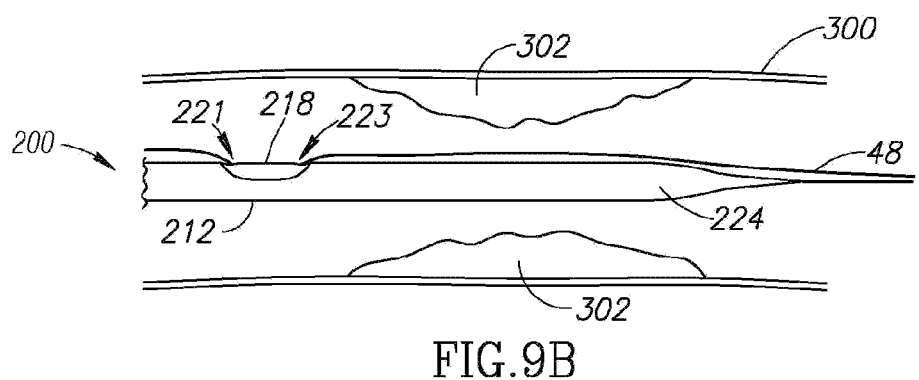
Figure 9C:
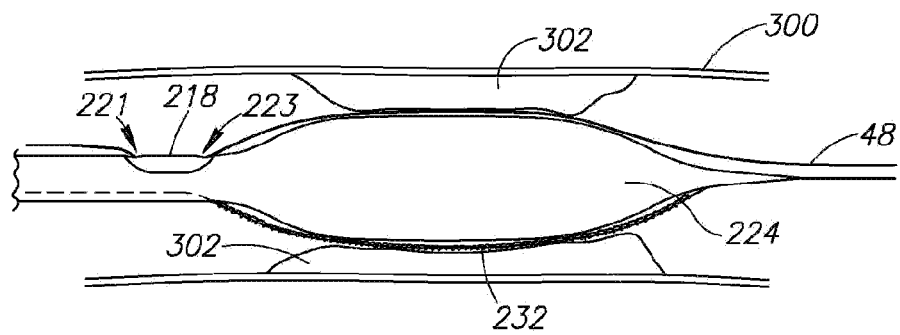

Reference is now made to FIGS. 9A-9C, which are schematic illustrations of the steps of a method of treating a vessel, in accordance with embodiments of the present invention. A vessel 300 having a lesion 302 is accessed via guidewire 48. Guidewire 48 is backloaded onto system 200 by placing guidewire 48 through auxiliary elongated element 218. Guidewire 48 exits through auxiliary elongated element proximal exit point 221, which may be relatively close to auxiliary elongated element distal exit point 223 for rapid exchange as shown in FIGS. 9B and 9C, or may be at the proximal end of main elongated element 212 for an over-the-wire configuration. System 200 is advanced over guidewire 48, and positioned such that balloon 224 is adjacent lesion 302, as shown in FIG. 9B. It should be noted that external core wire 232 is not shown in FIG. 9B during insertion, since it is folded into balloon 224. Balloon 224 is then inflated, as shown in FIG. 9C, which pushes both guidewire 48 and external core wire 232 up against lesion 302. The presence of guidewire 48 and/or external core wire 232 provides a focused force to enable the user to crack hard lesions at low pressure before balloon 224 is fully inflated. Doing so allows vessel stretching to occur at a lower strain rate, thus minimizing the trauma associated with balloon dilatation. Alternatively, instead of introducing a guidewire, fixed wire 240 is used to cross the lesion. In this embodiment, auxiliary elongated element 218 may optionally not be included. Balloon 224 is then expanded, and external core wire 232 provides the focused force. If auxiliary elongated element 218 is present, a guidewire 48 may additionally be introduced through auxiliary elongated element 218 to provide additional focused force. These forces may be useful in treating a variety of lesions, including those found at renal or peripheral vessels, and may be useful for procedures requiring high forces such as valvuloplasty. It should be readily apparent that when auxiliary elongated element 218 is included, it may also be used as a conduit to provide objects, treatment drugs, contrast media, guidewires, etc. to the vessel.

Figure 10A:
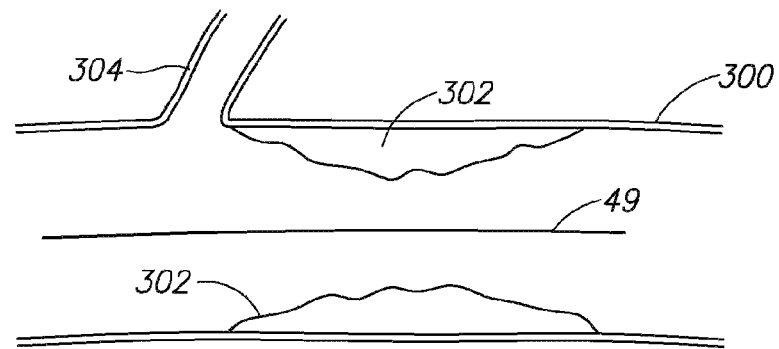
FIGS. 10A-10C are schematic illustrations of the steps of a method of treating a bifurcated vessel, in accordance with additional embodiments of the present invention.
Figure 10B:
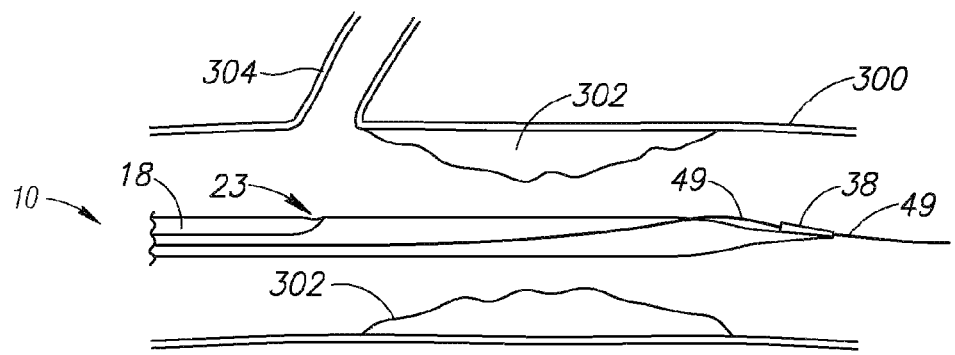
Figure 10C:
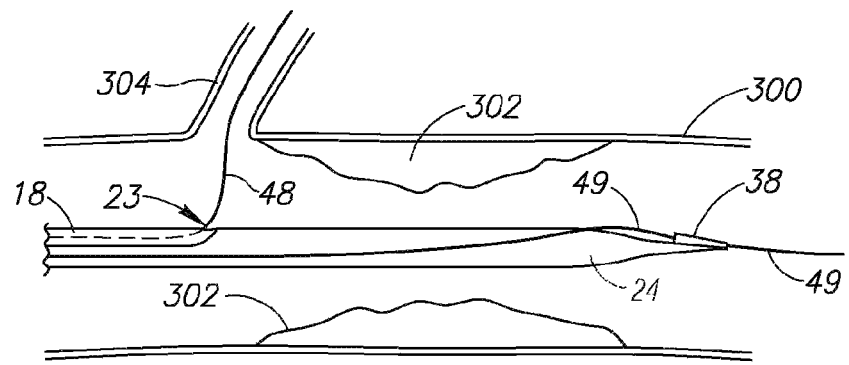

In some embodiments, the systems of the present invention may be used to treat vessels at a bifurcation. Reference is now made to FIGS. 10A-10C, which are schematic illustrations of the steps of a method for treating a bifurcated vessel, in accordance with embodiments of the present invention. First, tracking guidewire 49 is introduced into the main vessel 300, as shown in FIG. 10A. Next, system 10 is advanced over tracking guidewire 49 by backloading tracking guidewire 49 through distal connecting element 38, as shown in FIG. 10B. A guidewire 48 may then be advanced through auxiliary elongated element 18 and into a branch vessel 304. The main vessel lesion 302 may then be treated by inflating balloon 24, while branch vessel 304 is protected in case of plaque shift or additional lesion portions extending into branch vessel 304.

In alternative embodiments, system 100 is advanced over a guidewire 48 by backloading guidewire 48 into both distal connecting element 138 and auxiliary elongated element 118. After treatment of lesion 302 in main vessel 300, guidewire 48 may be pulled back proximally and introduced into branch vessel 304. The balloon is deflated, the catheter is retracted along the guidewire, and the system is introduced into the branch vessel. The balloon may then be reinflated so as to compress the lesion in the branch vessel. In an alternative method, the guidewire is introduced into the branch vessel, and the catheter is advanced over the guidewire past the bifurcation and into the main vessel. The main vessel lesion is then treated by inflating the balloon and compressing the lesion. The balloon is deflated, the catheter is retracted, and introduced into the branch vessel such that the guidewire is positioned alongside the balloon. Upon inflation of the balloon, the guidewire is compressed into the lesion site, and provides a focused force to enable the user to crack hard lesions at low pressure before the balloon is fully inflated. This alternative method is possible using system 200 with fixed wire 240, since fixed wire 240 may be used to cross the lesion at the main vessel while guidewire 48 is positioned in the branch vessel.

While certain features of the present invention have been illustrated and described herein, many modifications, substitutions, changes, and equivalents may occur to those of ordinary skill in the art. For example, a catheter for uses other than expansion of a balloon and/or delivery of a stent may be used with the device of the present invention, such as a catheter for drug delivery at an ostium, for cauterization, or for any other treatment. It is, therefore, to be understood that the appended claims are intended to cover all such modifications and changes as fall within the true spirit of the present invention.

Reference is now made to FIGS. 11A-11C, which are schematic illustrations of a system 400, in accordance with yet additional embodiments of the present invention. System 400 includes a main elongated element 412 having a proximal end 414 and a distal end 416. In some embodiments of the present invention, main elongated element 412 is a catheter shaft. A balloon 424 is positioned at distal end 416 of main elongated element 412. As shown in FIG. 11B, an interior portion of main elongated element 412 serves as an inflation lumen 426, providing fluid communication between an inflation port 452 located at proximal end 414 of main elongated element 412 and balloon 424 located at distal end 416 of main elongated element 412. Balloon 424 can be comprised of a variety of diameters, ranging from 1.25-10.0 mm, for example, and a variety of lengths, ranging from 10 mm to 30 cm, for example. Long balloons may be particularly useful for treating peripheral lesions, which often have long diseased portions. In one embodiment, an auxiliary elongated element may be included within and along a length of main elongated element 412 for positioning of a mandrel for increased rigidity and/or as an additional bonding area. System 400 further includes a sheath 470 coaxial to main elongated element 412. Sheath 470 has a proximal end 472 and a distal end 474. Proximal end 472 is positioned near a proximal end of system 400 and may include a handle or other means for moving sheath 470 via proximal end 472. Distal end 474 is positioned in a vicinity of balloon 424. Sheath 470 is movable proximally and distally, as shown by arrow 471 such that sheath 470 may surround all or some of balloon 424. Sheath 470 is thus designed to act as a sizer for balloon 424, wherein a position of sheath 470 will determine the size of balloon 424 to be expanded. Sheath 470 is shown in FIG. 11A in a proximal position, wherein all of or a majority of balloon 424 is exposed and may thus be expanded. Sheath 470 is shown in FIG. 11B in a more distal position, wherein a portion of balloon 424 is covered by sheath 470 and as such, upon expansion of balloon 424, only the portion distal to distal end 474 of sheath 470 will expand. This configuration is shown in FIG. 11C.

System 400 may further include a core wire 428, which provides enhanced pushability of system 400 without significantly reducing the flexibility of system 400. Core wire 428 may be provided in a flexible portion, and may terminate at a stiff portion when no longer needed for rigidity, as described above with respect to system 10 and FIGS. 1A-1G or may run along an entire length of main elongated element 412 if necessary. Core wire 428 may vary in diameter along the length so as to provide increased rigidity at proximal end 414. In some embodiments, the flexible shaft may also be braided or otherwise strengthened to provide sufficient rigidity. The core wire 428 may be unslidingly attached to the system 400 to provide the desired pushability.

In embodiments of the present invention, core wire 428 has a portion positioned within main elongated element 412, referred to herein as internal core wire portion 430, and a portion positioned external to main elongated element 412, referred to herein as external core wire portion 432. Internal core wire portion 430 is proximal to external core wire portion 432, and is attached to main elongated element 412 at an internal core wire attachment point 444. As discussed above with respect to FIG. 5A, external core wire portion 432 may be configured with a coil 434. For embodiments wherein main elongated element 412 is comprised of a relatively flexible distal portion and a relatively rigid proximal portion, internal core wire attachment point 444 is located at an interface between the stiff proximal portion and the flexible distal portion, for example, a distal end of the hypotube. In embodiments wherein main elongated element 412 is mostly or completely comprised of flexible material, internal core wire attachment point 444 is located at proximal end 414 of system 400. However, it should be readily apparent that internal core wire attachment point 444 may be located at any location along the length of main elongated element 412. Moreover, multiple internal core wire attachment points 444 may be included. The attachment point 444 may be any engagement between the core wire 428 and the system 400 that prevents the relative longitudinal movement of the core wire 428 relative to the system 400 at the attachment point 444. At a location proximal to balloon 424, internal core wire portion 430 exits main elongated element 412 and becomes external core wire portion 432. This location is referred to herein as a core wire exit point 442. In one embodiment, core wire exit point 442 is at a distal end of main elongated element 412. In other embodiments, core wire exit point 442 is at other locations along main elongated element 412 (but in most cases proximal to balloon 424). Distal to core wire exit point 442, external core wire portion 432 is positioned alongside balloon 424, and a distal end of external core wire portion 432 is attached to a distal tip 425 of balloon 424. Several attachment or bonding locations provide transmission of forces through the length of the catheter, and thus enhance overall torquability and rotatability. In particular, bonding can be done at any or all of the following locations: at distal tip 425 of balloon 424, at core wire exit point 442, and at internal core wire attachment point 444. Additional attachment points may be included as well. It should be noted that the use of an internal core wire makes it possible to have a longer flexible (polymeric or other) portion or even a completely flexible shaft, enhancing overall flexibility of system 400.

System 400 further includes a distal connecting element 438 at distal tip 425 of balloon 424. Distal connecting element 438 is a short rail, ranging in length from 2-25 mm, and may be bonded to distal tip 425 such that the proximal end of distal connecting element 438 is distal to balloon 424. A three-way bond may be used to attach distal connecting element 438, balloon 424 and external core wire portion 432, all together.

Distal connecting element 438 may be tapered toward its distal end to facilitate passage through tight stenoses. In some embodiments, distal connecting element 438 is positioned at a rotational distance from external core wire portion 432, and is generally cylindrically shaped to hold a tracking guidewire 49 therethrough. In this way, tracking guidewire 49 and core wire 432 may both lie alongside balloon 424 at different rotational positions along balloon 424 when balloon 424 is in its expanded state. Although the separation between tracking guidewire 49 and core wire 432 is not required to be any specific amount, it should be apparent that the distance between them should be sufficient to provide separate wires alongside different areas of balloon 424. Each of these wires can then provide a focused force to help crack difficult lesions, as will be explained further hereinbelow.

It is a particular feature of the present invention, that by tracking system 400 over tracking guidewire 49, which is positioned within distal connecting element 438, rapid exchange capabilities are maintained. The rapid exchange capability, along with a variable length balloon whose length is controlled via an outer sheath, is particularly advantageous and had previously not been contemplated since rapid exchange catheters generally have a tracking guidewire exit point along a length of the catheter, and this exit point would tend to be trapped by an outer sheath such as the one described herein.

Reference is now made to FIG. 11D, which is a cross-sectional illustration of system 400 shown at section A-A, in accordance with embodiments of the present invention. Sheath 470 surrounds main elongated element 412. Tracking guidewire 49 is outside of sheath 470. An inflation lumen 426 may be an interior portion of main elongated element 412, with core wire 430 positioned therein.

Figure 12A:
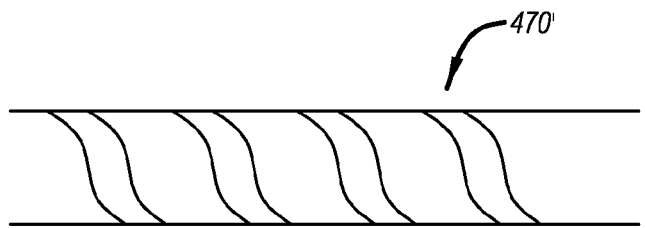
FIGS. 12A and 12B are illustrations of the sheath of FIGS. 11A-11D, in accordance with embodiments of the present invention.
Figure 12B:
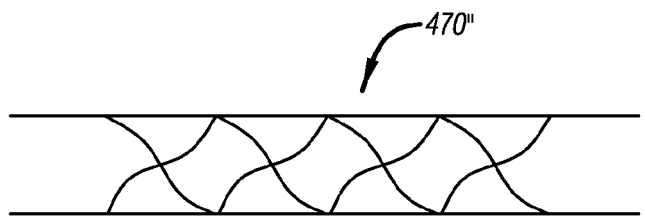

Reference is now made to FIGS. 12A-12B, which are schematic illustrations of sheath 470 in accordance with embodiments of the present invention. Sheath 470 must be constructed such that it is strong enough to resist forces generated by inflation of balloon 424. Thus, sheath 470' may be comprised of coiled material, as in FIG. 12A, sheath 470" may be comprised of a braided material, as in FIG. 12B, or any other suitable material for providing sufficient resistance while still retaining flexibility. In some embodiments, sheath 470 may include a polymeric liner or outer jacket in order to provide additional strength.

Figure 13:
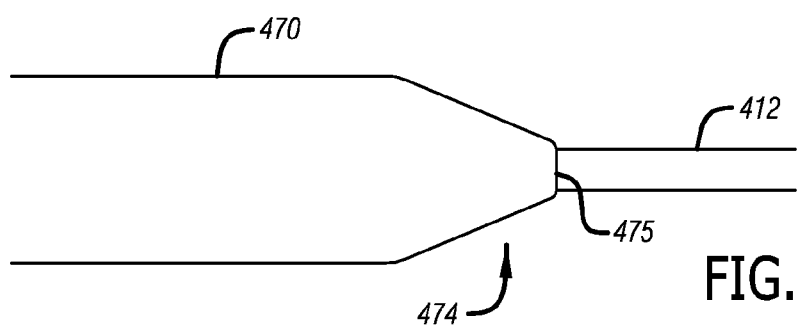
FIG. 13 is an illustration of an edge of the sheath of FIGS. 11A-11D.

Distal end 474 of sheath 470 includes an edge 475. In order to avoid intimal damage during insertion and movement of sheath 470, edge 475 may be tapered, as shown in FIG. 13. In some embodiments, a hydrogel may be applied to either balloon 424 or an interior portion of sheath 470 for lubrication. In one embodiment, a soft edge may be used. In one embodiment, sheath 470 may be initially positioned in its most distal position, covering all of balloon 424, so that during insertion the risk of intimal damage is minimized. In this embodiment, sheath 470 is then retracted upon arrival at the treatment site, so as to expose the desired balloon length.

Figure 14:
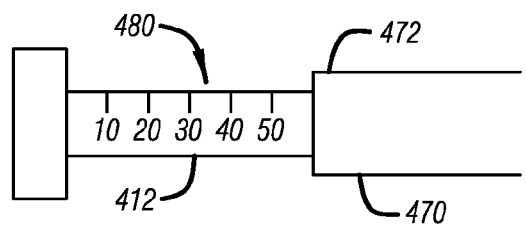
FIG. 14 is an illustration of a proximal end of the system of FIGS. 11A-11D.

Reference is now made to FIG. 14, which is an illustration of proximal end 472 of sheath 470. Main elongated element 412 includes markings 480, which allows for controlled positioning of sheath 470 with respect to balloon 424. In some embodiments, a ratchet type system may be included at proximal end 414 for control of sheath 470 so as to provide more specific control over distances in incremental stages.

Figure 15A:
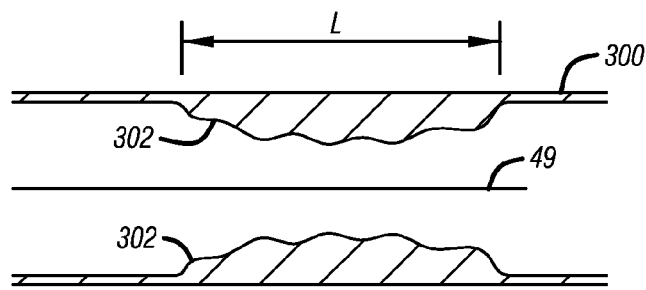
FIGS. 15A-15D are illustrations of the steps of a method of treating a vessel, in accordance with additional embodiments of the present invention.
Figure 15B:
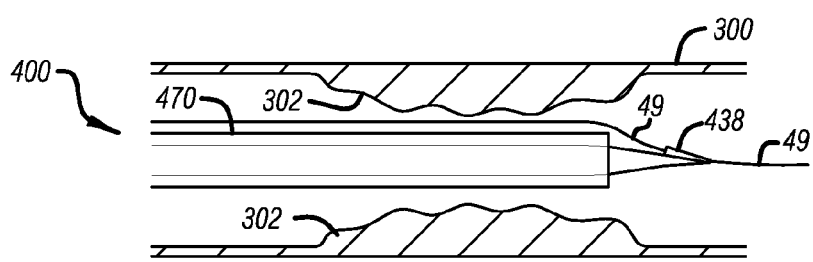
Figure 15C:
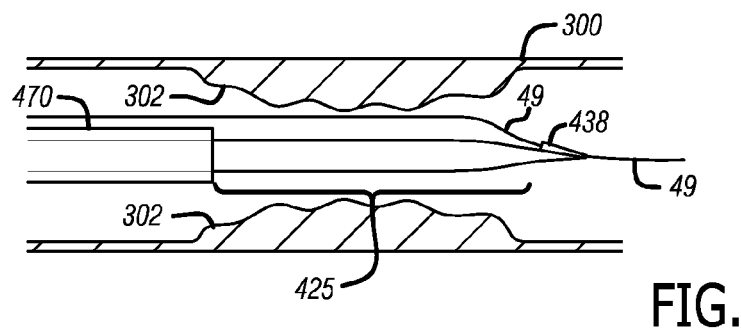
Figure 15D:
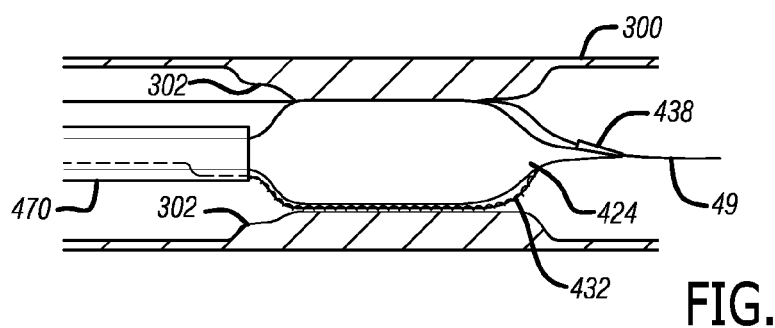

Reference is now made to FIGS. 15A-15D, which are schematic illustrations of the steps of a method of treating a vessel, in accordance with embodiments of the present invention. A vessel 300 having a lesion 302 of length L is accessed via tracking guidewire 49 as shown in FIG. 7A. Tracking guidewire 49 is backloaded onto system 400 by placing tracking guidewire 49 through distal connecting element 438, and system 400 is advanced over tracking guidewire 49 to the vicinity of lesion 302, as shown in FIG. 15B. System 400 may then be pulled back proximally so that tracking guidewire 49 is adjacent balloon 424 and is in a vicinity of lesion 302. Sheath 470 is then pulled back proximally, thereby providing an exposed portion 425 of balloon 424, wherein exposed portion 425 is of a length suitable for treating lesion 302 of length L. The length of exposed portion 425 may be controlled at a proximal end of system 400 using markings 480 as described with respect to FIG. 14. Exposed portion 425 of balloon 424 is then expanded by inflating balloon 424, as shown in FIG. 15D. It should be readily apparent that a strength of sheath 470 prevents portions of balloon 424 within sheath 470 from also being expanded. In some embodiments, system 400 may be removed and exchanged with another catheter or catheter system using a rapid exchange method, wherein system 400 is removed proximally along tracking guidewire 49 and the other catheter or catheter system is introduced over tracking guidewire 49.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A device for introduction into a vessel, comprising:
a main elongated element having a main elongated element proximal end and a main elongated element distal end;
a balloon positioned at the main elongated element distal end, the balloon having a balloon proximal end, a balloon distal end, and an inflation lumen therethrough;
a distal connecting element positioned at the distal end of the balloon to receive a guidewire during use; and
a longitudinally movable sheath positioned external to the main elongated element, the longitudinally movable sheath having a distal end and a proximal end, wherein the distal end of the sheath includes a tapered end with a soft edge that expands upon retraction of the sheath over the balloon, and wherein a position of the sheath distal end with respect to the balloon defines an exposed portion of the balloon that expands when fluid is delivered to the balloon through the inflation lumen.

2. The device according to claim 1, further comprising a tracking guidewire for advancement of the device into the vessel, the tracking guidewire positioned through the distal connecting element, wherein the distal connecting element is a generally cylindrical rail attached to the balloon distal end.

3. The device according to claim 1, further comprising a core wire unslidingly attached to the main elongated element at a core wire attachment point, the core wire including an internal core wire portion positioned within the main elongated element and an external core wire portion positioned distally with respect to the internal core wire portion, the external core wire portion external to and running alongside the balloon.

4. The device according to claim 3, wherein the distal connecting element is at a rotational distance from the external core wire portion of the core wire.

5. The device according to claim 3, the device further comprising a first radiopaque marker and a second radiopaque marker on the core wire along a first longitudinal axis, and a third radiopaque marker on a second longitudinal axis different from the first longitudinal axis.

6. The device according to claim 3, wherein the external core wire portion further comprises a coil wrapped around at least a portion thereof, the coil-wrapped portion positioned adjacent to the balloon, and at least one radiopaque marker on the external core wire portion.

7. The device according to claim 1, wherein the sheath comprises a braided material to prevent an unexposed portion of the balloon from expanding when the sheath is positioned external to the unexposed portion of the balloon.

8. The device according to claim 1, wherein the sheath comprises a helical coil to prevent an unexposed portion of the balloon from expanding when the sheath is positioned external to the unexposed portion of the balloon.

9. The device according to claim 1, further comprising an auxiliary elongate element proximal to the balloon within a portion of the main elongate element and aligned with the distal connecting element, and a core wire attached to the auxiliary elongate element.

10. The device according to claim 1, further comprising a handle at a proximal end of the sheath for longitudinally positioning the sheath with respect to the balloon.

11. The device according to claim 10, wherein the handle includes markings to indicate the sheath retraction and provide a length of the exposed portion of the balloon.

12. A device for introduction into a vessel, comprising:
a main elongated element having a main elongated element proximal end and a main elongated element distal end;
a balloon positioned at the main elongated element distal end, the balloon having a balloon proximal end, a balloon distal end, and an inflation lumen therethrough;
a distal connecting element positioned at the distal end of the balloon to receive a guidewire during use;
a longitudinally movable sheath positioned external to the main elongated element, the longitudinally movable sheath having a distal end and a proximal end, wherein a position of the sheath distal end with respect to the balloon defines an exposed portion of the balloon that expands when fluid is delivered to the balloon through the inflation lumen; and
a handle at a proximal end of the sheath for longitudinally positioning the sheath with respect to the balloon.

13. The device according to claim 12, further comprising a tracking guidewire for advancement of the device into the vessel, the tracking guidewire positioned through the distal connecting element, wherein the distal connecting element is a generally cylindrical rail attached to the balloon distal end.

14. The device according to claim 12, further comprising a core wire unslidingly attached to the main elongated element at a core wire attachment point, the core wire including an internal core wire portion positioned within the main elongated element and an external core wire portion positioned distally with respect to the internal core wire portion, the external core wire portion external to and running alongside the balloon.

15. The device according to claim 14, wherein the distal connecting element is at a rotational distance from the external core wire portion of the core wire.

16. The device according to claim 14, the device further comprising a first radiopaque marker and a second radiopaque marker on the core wire along a first longitudinal axis, and a third radiopaque marker on a second longitudinal axis different from the first longitudinal axis.

17. The device according to claim 14, wherein the external core wire portion further comprises a coil wrapped around at least a portion thereof, the coil-wrapped portion positioned adjacent to the balloon, and at least one radiopaque marker on the external core wire portion.

18. The device according to claim 12, wherein a distal end of the sheath includes a tapered end with a soft edge that expands upon retraction of the sheath over the balloon.

19. The device according to claim 12, wherein the sheath comprises a braided material to prevent an unexposed portion of the balloon from expanding when the sheath is positioned external to the unexposed portion of the balloon.

20. The device according to claim 12, wherein the sheath comprises a helical coil to prevent an unexposed portion of the balloon from expanding when the sheath is positioned external to the unexposed portion of the balloon.

21. The device according to claim 12, further comprising an auxiliary elongate element proximal to the balloon within a portion of the main elongate element and aligned with the distal connecting element, and a core wire attached to the auxiliary elongate element.

22. The device according to claim 12, wherein the handle includes markings to indicate the sheath retraction and provide a length of the exposed portion of the balloon.

23. A device for introduction into a vessel, comprising:
a main elongated element having a main elongated element proximal end and a main elongated element distal end;
a balloon positioned at the main elongated element distal end, the balloon having a balloon proximal end, a balloon distal end, and an inflation lumen therethrough;
a distal connecting element positioned at the distal end of the balloon to receive a guidewire during use;
an auxiliary elongate element proximal to the balloon within a portion of the main elongate element and aligned with the distal connecting element;
a core wire attached to the auxiliary elongate element; and
a longitudinally movable sheath positioned external to the main elongated element, the longitudinally movable sheath having a distal end and a proximal end, wherein a position of the sheath distal end with respect to the balloon defines an exposed portion of the balloon that expands when fluid is delivered to the balloon through the inflation lumen.

* * * * *